(12) United States Patent
De Bruijn et al.

(10) Patent No.: US 10,883,122 B2
(45) Date of Patent: Jan. 5, 2021

(54) FERMENTATION PROCESS FOR IMPROVED GLYCEROL AND ACETIC ACID CONVERSION

(71) Applicant: DSM IP ASSETS B.V., Heerlen (NL)

(72) Inventors: Hans Marinus Charles Johannes De Bruijn, Echt (NL); Wilhelmus Theodorus Antonius Maria De Laat, Echt (NL); Paul Klaassen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/535,961

(22) PCT Filed: Dec. 17, 2015

(86) PCT No.: PCT/EP2015/080330
§ 371 (c)(1),
(2) Date: Jun. 14, 2017

(87) PCT Pub. No.: WO2016/097202
PCT Pub. Date: Jun. 23, 2016

(65) Prior Publication Data
US 2017/0335350 A1    Nov. 23, 2017

(30) Foreign Application Priority Data
Dec. 19, 2014  (EP) .................................... 14199434

(51) Int. Cl.
*C12P 7/10* (2006.01)
*C12P 7/06* (2006.01)
*C07C 31/08* (2006.01)

(52) U.S. Cl.
CPC ................ *C12P 7/10* (2013.01); *C07C 31/08* (2013.01); *C12P 7/06* (2013.01); *C12Y 101/01006* (2013.01); *C12Y 102/0101* (2013.01); *C12Y 207/01028* (2013.01); *C12Y 207/01029* (2013.01); *C12Y 602/01001* (2013.01); *Y02E 50/10* (2013.01)

(58) Field of Classification Search
None
See application file for complete search history.

(56) References Cited

U.S. PATENT DOCUMENTS

| 2015/0176032 A1 | 6/2015 | De Bont |
| 2015/0252319 A1 | 9/2015 | De Bruun |
| 2016/0208291 A1 | 7/2016 | Klaassen |

FOREIGN PATENT DOCUMENTS

| WO | 2011149353 A1 | 12/2011 |
| WO | 2012067510 A1 | 5/2012 |
| WO | 2013081456 A2 | 6/2013 |
| WO | 2014072232 A1 | 5/2014 |
| WO | 2014180820 A2 | 11/2014 |
| WO | 2015028582 A2 | 3/2015 |
| WO | 2015028583 A2 | 3/2015 |

OTHER PUBLICATIONS

Yu et al., "Improvement of Ethanol Yield from Glycerol via Conversion of Pyruvate to Ethanol in Metabolically Engineered *Saccharomyces cerevisiae*" Appl Biochem Biotechnol. (2012) vol. 166: 856-865.
Yu et al., "Engineering of glycerol utilization pathway for ethanol production by *Saccharomyces cerevisiae*" Biosiyrce Technology. (2010) p. 4157-4161.
Van Dijken et al., "Redox balances in the metabolism of sugars by yeast" FEMS Icrobiology Reviews. (1986) p. 199-224.
Sonderegger et al., "Metabolic Engineering of a Phosphoketolase Pathway for Pentose Catabolism in *Saccharomyces cerevisiae*" Environmental Microbiology (May 2004) p. 2892-2897.
Medina et al., "Elimination of Glycerol Production in Anaerobic Cultures of a *Saccharomyces cerevisiae* Strain Engineered to Use Acetic Acid as an Electron Acceptor" Applied and Environmental Microbiology. (Jan. 2010) vol. 76, No. 1:190-195.
Luttik et al., "The *Saccharomyces cerevisiae* ICL2 Gene Encodes a Mitochondrial 2-Methylisocitrate Lyase Involved in Propionyl-Coenzyme A Metabolism" Journal of Bacteriology. (Dec. 2000) vol. 182, No. 24:7007-7013.
Lee et al., "Application of sequential integration for metabolic engineering of 1,2-propanediol production in yeast" Metabolic Engineering. (2006) p. 58-65.

*Primary Examiner* — Iqbal H Chowdhury
(74) *Attorney, Agent, or Firm* — McBee Moore & Vanik IP, LLC

(57) ABSTRACT

The invention relates to a process for producing a fermentation product that comprises fermentation of a carbon source in a reactor with a cell, capable of converting sugar, glycerol and acetic acid, wherein the carbon source comprises sugar and acetic acid, comprising the following steps:
  a) Inoculating a optionally diluted carbon source with the cell;
  b) optionally fermenting the reactor in batch mode;
  c) adding carbon source comprising glycerol and optionally sugar gradually to the reactor;
  d) after sufficient fermentation time, isolation of fermentation product from the reactor,
  e) optionally keeping the remaining fraction after isolation of step d) as spent broth; and
  f) optionally using the spent broth in step a) to dilute the carbon source.

18 Claims, 35 Drawing Sheets

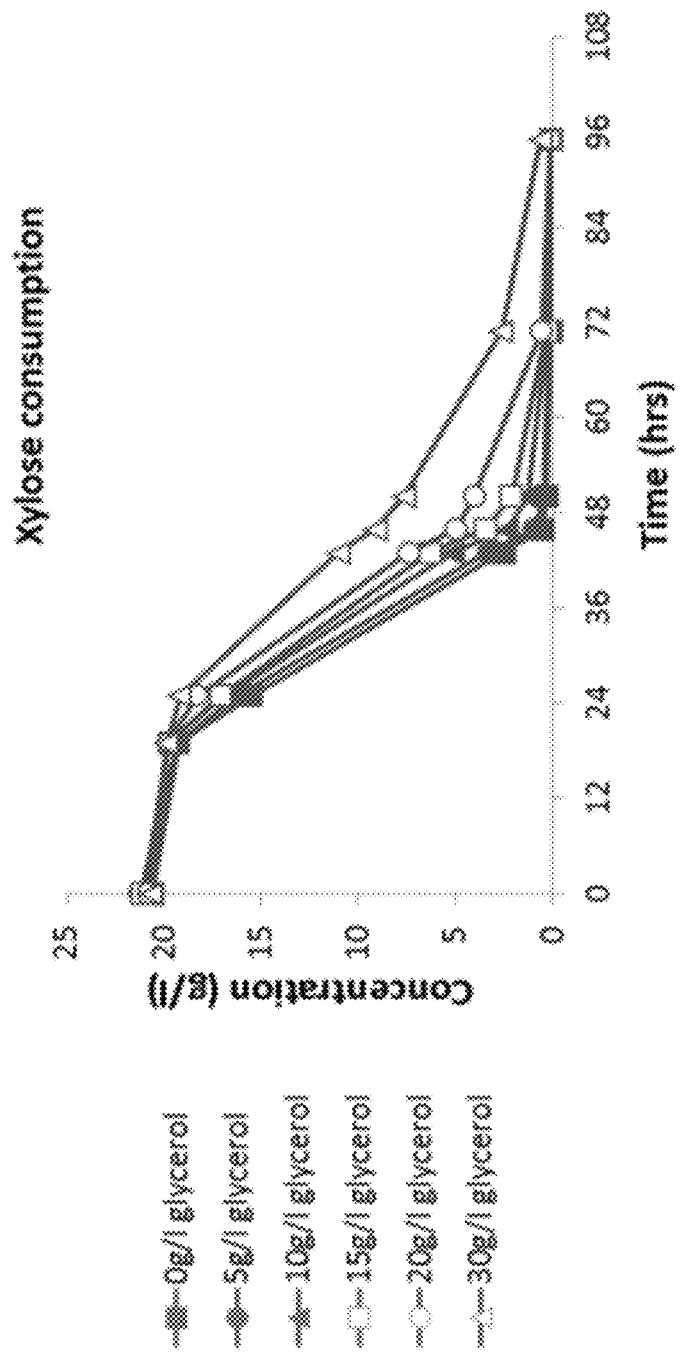

Fig. 4 (cntd)
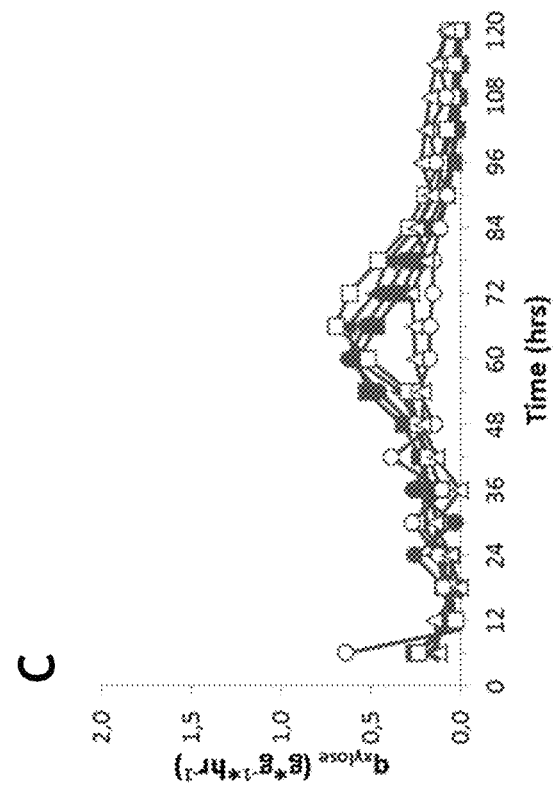
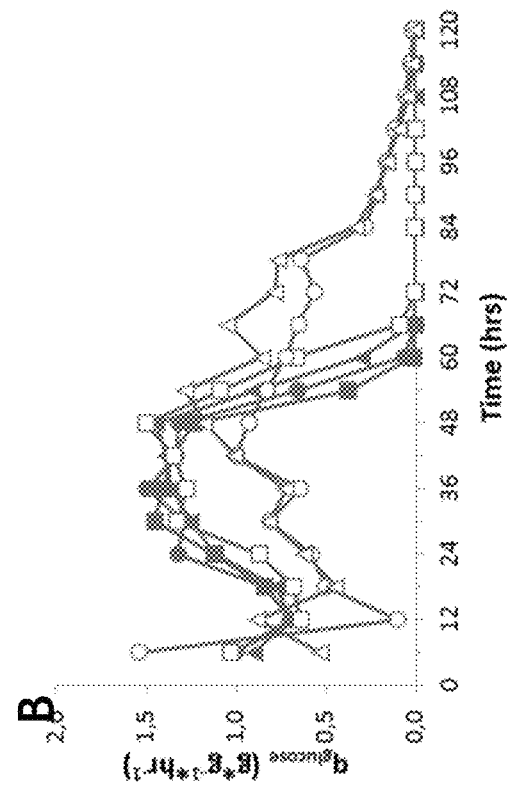

Fig. 8 (A, B)
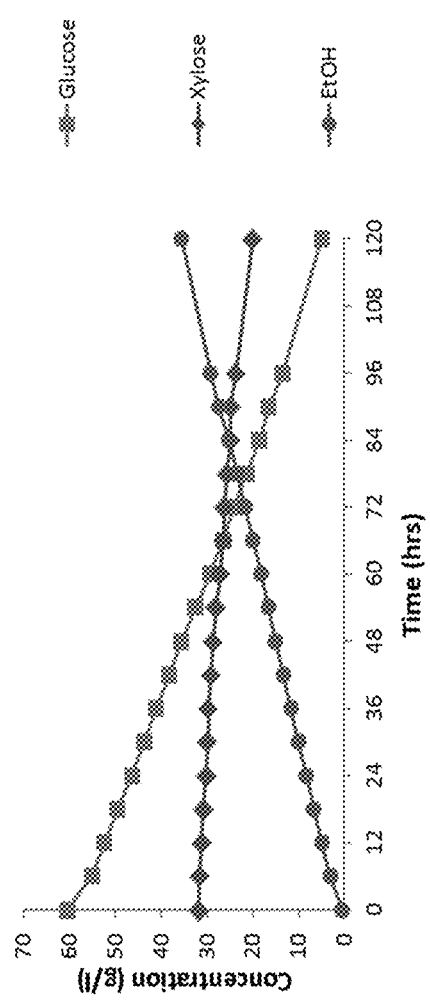
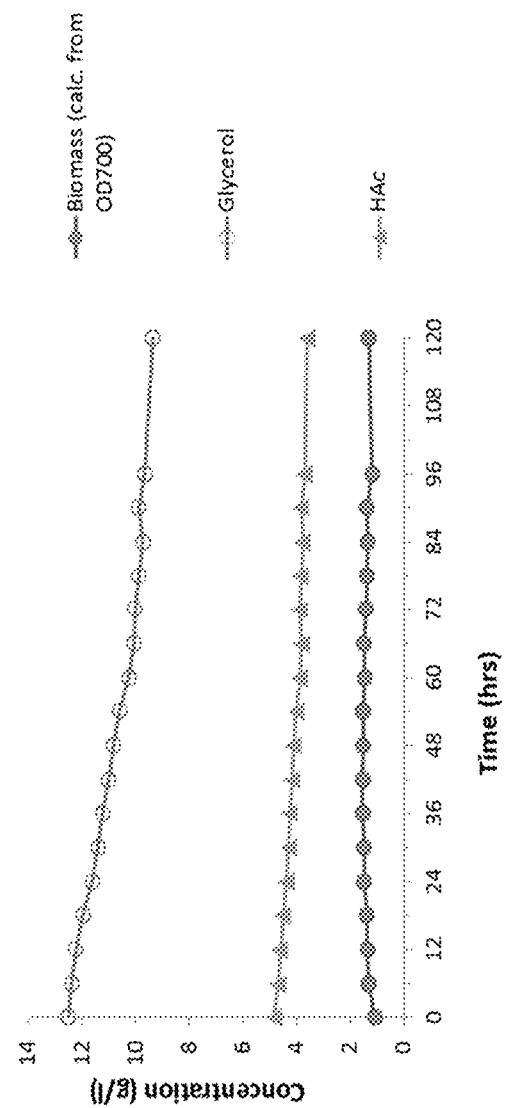
8A
8B

Fig. 9
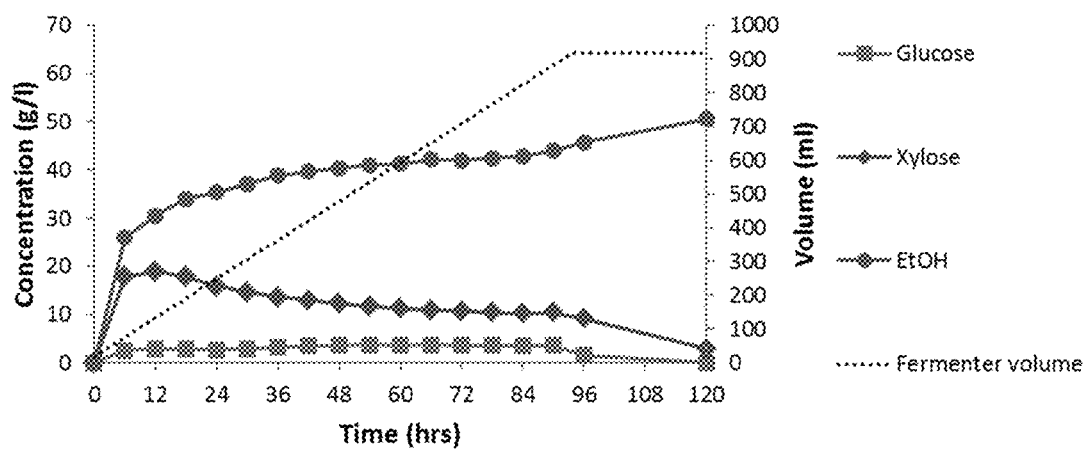
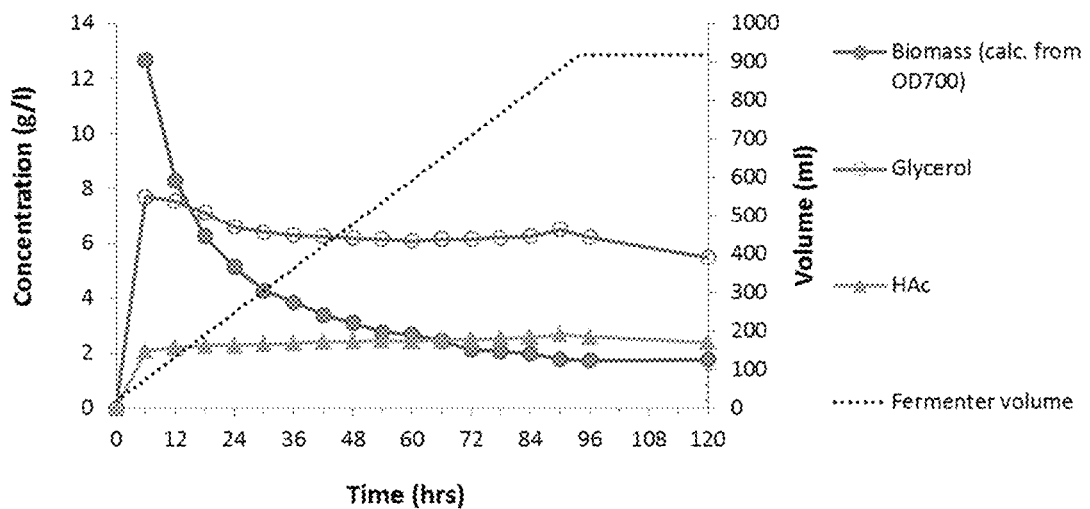

FERMENTATION PROCESS FOR IMPROVED GLYCEROL AND ACETIC ACID CONVERSION

CROSS-REFERENCE TO RELATED APPLICATIONS

This application is a National Stage entry of International Application No. PCT/EP2015/080330 filed 17 Dec. 2015, which claims priority to European Patent Application No. 14199434.3, filed 19 Dec. 2014.

FIELD OF THE INVENTION

The present invention relates to a fermentation process. In particular the invention relates fermentation process with glycerol and acetic acid converting yeast cells with improved acetic acid conversion. The invention further relates to the processes wherein the yeast cells produce fermentation product, such as ethanol.

BACKGROUND OF THE INVENTION

Second generation bioethanol is produced from e.g. lignocellulosic fractions of plant biomass that is hydrolyzed into free monomeric sugars, such as hexoses and pentoses, for fermentation into ethanol. Apart from the sugar release during pretreatment and hydrolysis of the biomass, some toxic by-products are formed. For instance, furfural and HMF are two of these products. The quantities in which they are formed depend on several pretreatment parameters, such as temperature, pressure and pretreatment time.
Lignocellulosic hydrolysates also contain high amounts of acetic acid, which is a potent inhibitor of the fermentative capacity of microorganisms, such as yeasts.

Glycerol is the major by-product during fermentation of sugars into ethanol, mainly formed as a result of re-oxidation reactions to consume the excess NADH formed during biosynthesis under anaerobic conditions (van Dijken and Scheffers, 1986). As a result, during industrial fermentations, about 5 to 10% of the consumed sugars by yeast cells are diverted into glycerol. Lowering the amount of this polyol is considered a promising route to increase ethanol yield. This could be achieved by adjusting the feeding rate during the fed-batch process, or by selecting strains that produce less glycerol.

In the literature, however, several different approaches have been reported that could help to reduce the inhibitory effect of acetic acid on the fermentation of the sugars in hydrolysates as well as (partly) solving redox balance issues upon deletion of the genes involved in glycerol production, e.g. by genetic engineering of yeasts.

Sonderegger et al (2004) disclosed the heterologous expression of phosphotransacetylase and acetaldehyde dehydrogenase in a xylose-fermenting *Saccharomyces cerevisiae* strain. In combination with the native phosphoketolase, Sonderegger et al thereby created a functional phosphoketolase pathway that is capable of net reoxidation of NADH generated by the heterologous expression of a xylose reductase and xylitol dehydrogenase that are used for xylose utilization in that particular strain.

Guadelupe et al (2010) described a *Saccharomyces cerevisiae* strain wherein production of the by-product glycerol is eliminated by the disruption of the endogenous NAD-dependent glycerol 3-phosphate dehydrogenase genes (GPD1 and GPD2). Expression of the *E. coli* mhpF gene, encoding the acetylating NAD-dependent acetaldehyde dehydrogenase, restored the ability of the gpd1gpd2 double deletion strain to grow anaerobically by supplementation of the medium with acetic acid.

Yu et al (2010) constructed *Saccharomyces cerevisiae* strains metabolically engineered for improved ethanol production from glycerol by simultaneous overexpression of glycerol dehydrogenase (encoded by GCY1), dihydroxyacetone kinase (DAK1) and the glycerol uptake protein (GUP1). In a later report by the same group (Yu et al, 2012) it is described that additional overexpression of ADH1 and PDC1, encoding alcohol dehydrogenase and pyruvate decarboxylase respectively, caused an increase in growth rate and glycerol consumption under fermentative conditions, resulting in a slightly increased final ethanol yield.

Lee and Dasilva (2006) disclosed the yeast *Saccharomyces cerevisiae* engineered to produce 1,2-propanediol from glycerol by amongst others introducing expression of the *Escherichia coli* mgs and gldA genes.

The technology described by Guadelupe et al (2010) (and also in patent application WO 2011/010923) provides a solution for decreasing the acetic acid content of hydrolysates during fermentation of the biomass sugars and the aforementioned acetic acid into e.g. ethanol.

Further enhancement of the ability to convert acetic acid is potentially possible by introducing an extra NADH-generating pathway, e.g. by additionally (over-)expressing a glycerol consumption pathway. Upon introduction of the aforementioned GUP1-, GCY1- and DAK1-genes (Yu et al, 2010) in a yeast strain expressing an anaerobic acetic acid conversion pathway (such as e.g. described by Medina et al, 2009), acetic acid conversion should be increased in order to maintain the redox balance, leading to further increased detoxification of the hydrolysate and higher ethanol yield. The solution of Yu et al however, does not work, since the yeast glycerol dehydrogenase (encoded by GCY1) uses $NADP^+$ as a co-factor, resulting in a cofactor imbalance due to insufficient cofactor regeneration. An alternative glyceroldehydrogenase (gldA from *E. coli*) was tested in combination with the acetic acid reduction pathway and indeed enhanced the conversion of acetic acid under anaerobic growth (fermentation) conditions (patent application WO2013/081456).

A disadvantage of the known processes is that the known batch fermentations of certain lignocellulosic hydrolysates with high toxicity (for instance with 2 g/l acetic acid or more) are not feasible with glycerol/HAc-converting yeast strains. This was found by us herein in and is described in the examples.

SUMMARY OF THE INVENTION

An objective of the invention is therefore to provide a feasible process for fermentation of lignocellulosic hydrolysates with high toxicity. Another object of the invention is to provide a process with efficient glycerol and HAc conversions. Another object is to provide a process wherein the strain has increased sugar conversion rate and improved cell growth.

One or more of these objectives are reached according to the invention, that provides a process for producing a fermentation product that comprises fermentation of a carbon source in a reactor with a cell, capable of converting sugar, glycerol and acetic acid, wherein the carbon source comprises sugar and acetic acid, comprising the following steps:
  a) Inoculating a optionally diluted carbon source with the cell;

b) optionally fermenting the reactor in batch mode;
c) adding carbon source comprising glycerol and optionally sugar gradually to the reactor;
d) after sufficient fermentation time, isolation of fermentation product from the reactor,
e) optionally keeping the remaining fraction after isolation of step d) as spent broth; and
f) optionally using the spent broth in step a) to dilute the carbon source.

As is shown in examples, the objectives are achieved.

BRIEF DESCRIPTION OF THE DRAWINGS

FIG. 8 Batch Fermentation of YD01437 on (NREL) pretreated corn stover hydrolysate supplemented with glycerol; Sugar conversion and EtOH production (A), glycerol- and HAc conversion, biomass (calculated from OD700) (B);

FIG. 9 Fed-batch Fermentation of YD01437 on (NREL) pretreated corn stover hydrolysate supplemented with glycerol; Sugar conversion and EtOH production (A), glycerol- and HAc conversion, biomass (calculated from OD700) (B);

DETAILED DESCRIPTION OF A PREFERRED EMBODIMENT

Figure 1A:
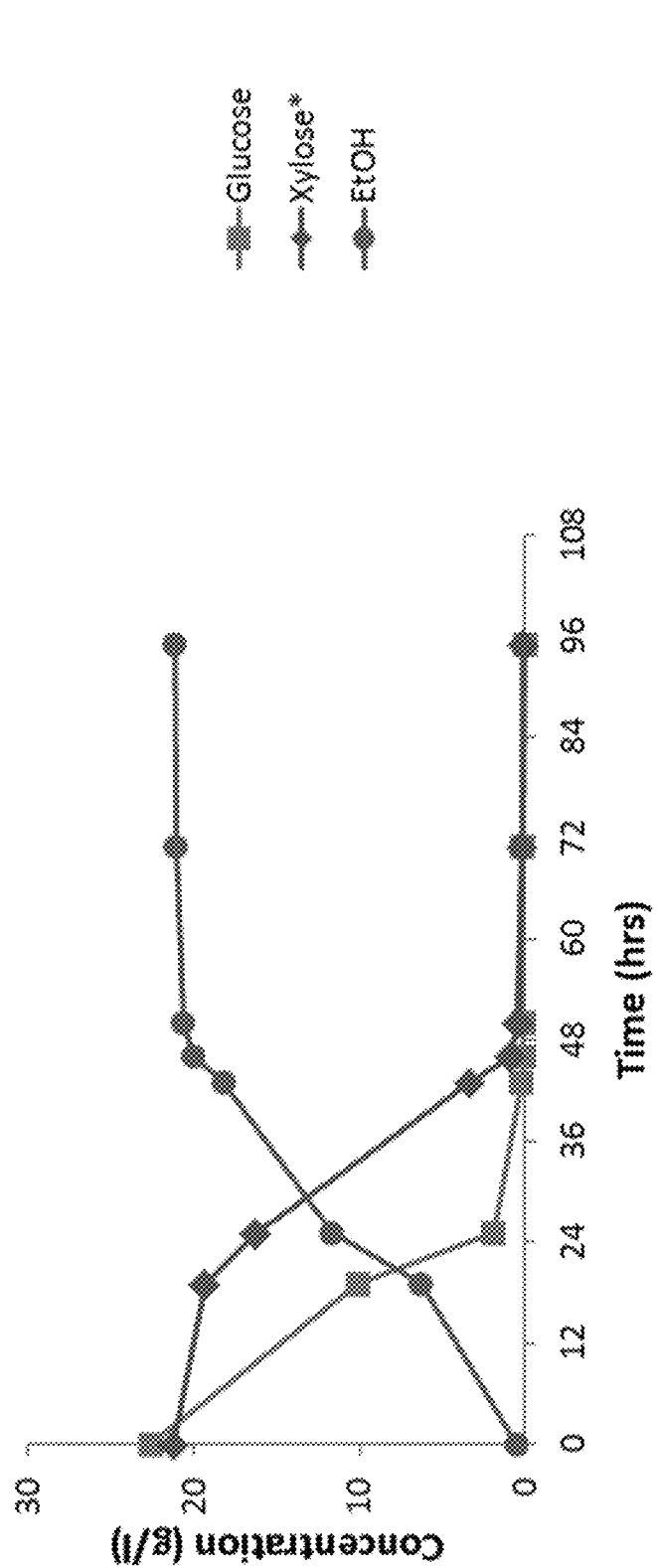
FIG. 1 Fermentation behavior of YD01248 on synthetic medium; Sugar conversion and EtOH production (A), glycerol- and HAc conversion, biomass(B)

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

The invention thus relates to a process for producing a fermentation product that comprises fermentation of a carbon source in a reactor with a cell, capable of converting sugar, glycerol and acetic acid, wherein the carbon source comprises sugar and acetic acid, comprising the following steps:
a) Inoculating a optionally diluted carbon source with the cell;
b) optionally fermenting the reactor in batch mode;
c) adding carbon source comprising glycerol and optionally sugar gradually to the reactor;
d) after sufficient fermentation time, isolation of fermentation product from the reactor,
e) optionally keeping the remaining fraction after isolation of step d) as spent broth; and
f) optionally using the spent broth in step a) to dilute the carbon source.

As is shown in the examples, with the process according to the invention, a feasible process for fermentation of lignocellulosic hydrolysates with high toxicity is achieved. Also a process with efficient glycerol and HAc conversions is achieved. Further in the process the strain has increased sugar conversion rate and improved cell growth. Additionally a unique feature of a fermented broth from a fermentation process according to the invention, is that it has a significantly reduced HAc content (compared to the unfermented hydrolysate or prior art product). This allows (part or whole of) the fermented broth, or distilled fermentation broth (stillage) to be recycled into the batch-phases of subsequent propagation and fermentation cycles without introducing inhibitory concentrations of HAc. In an embodiment for instance a liquid fraction of stillage to use as dilution water before and/or after pretreatment. In an embodiment, this allows recycling of enzyme used in the hydrolysis of lignocellulosic material, when using heat-stable enzymes that survive distillation.

Embodiment of the process of the invention are described in more detail here:

Step a) may involve filling the reactor with the carbon source. This may be done in any conventional way. The reactor may be filled partly or fully. The filling may be metered. In this stage temperature may be changed e.g. by heating or cooling. The carbon source may be an aqueous liquid, an aqueous slurry. The aqueous liquid may comprise any carbon source the cell can use, e.g. hexose or pentose sugar, e.g. glucose, xylose and/or arabinose. In an embodiment the carbon source is a lignocellulose hydrolysate. Further in an embodiment of step a), the carbon source may optionally be diluted with a liquid comprising 2 g/l or less acetic acid. Since the carbon source may be toxic to the cell, in this step the contents of the reactor may be diluted if it is too toxic for the microorganism. The dilution may be done in any conventional way, by adding a dilutant e.g. (process) water. The dilution may be metered.

This process step may be conducted in conventional way, though some parameters of these steps may be different then in the specific known conventional processes as in described in more detail below.

In step a) any suitable carbon source may be used. In an embodiment, in step a), the carbon source may be diluted lignocellulosic hydrolysate, more specifically lignocellulosic hydrolysate that is two or more fold diluted in water. In step a) cells are added to the reactor. Adding of a cell e.g. as a cell population to the contents of the reactor (inoculation), is conducted in a known manner. The cell population may be added as dry cell mass, as a cream, or suspended in water.

Steps of adding carbon source to the reactor, dilution of the carbon source and inoculation may also be executed in any other way of bringing the carbon source, diluent, and initial cell together, into e.g. carbon source and diluent may be combined in another vessel than the reactor, for later use in the reactor.

b) optionally fermenting the initial cell population in the reactor in batch mode. In this optional step, fermentation of the initial cell population is conducted in known manner, under conditions, so that carbon source is used for growth of the cells and/or for production of fermentation product.

c) adding carbon source comprising glycerol and optionally sugar gradually to the reactor;

In this step carbon source comprising glycerol and optionally sugar is gradually added to the reactor.

The present invention allows the use of 1$^{st}$ generation ethanol plant stillage as a glycerol source in ethanolic fermentation. Therefore in an embodiment, 1$^{st}$ gen stillage is added to the fermentation medium.

Range of dry matter contents at which stillage which may be used is common, e.g. 10-60 wt % or 20-40wt %. Glycerol concentration may typically range from 15 g/l to 200 g/l, e.g. 80-120 g/l or about 100 g/l.

In one embodiment of the invention glycerol derived from transesterification-based biodiesel processes in ethanolic fermentation is used as glycerol source.

In an embodiment, glycerol is added after glucose is substantially depleted, e.g. when the glucose concentration is 2 g/l or lower or after glucose depletion.

In an embodiment, the amount of glycerol added is such that the molar concentration of glycerol in the reactor is about twice the molar concentration of acetic acid in the reactor. For instance the molar concentration of glycerol in the reactor may be 1,8-2,2 times the molar concentration of acetic acid in the reactor. In an embodiment, the added glycerol originates from a starch based or sucrose based ethanol production plant.

In an embodiment, the added glycerol originates from a transesterification-based biodiesel production plant.

In an embodiment, the addition of glycerol is commenced when the glucose concentration in reactor is 2 g/l or lower.

Addition of glycerol source to hydrolysate or hydrolysate feed so that concentration glycerol is in a certain range, e.g. <8 g/l (see Combative experiment C) for 17% ds pCS, this may be higher for hydrolysates at higher % ds. In an embodiment the concentration is such that mol glycerol=mol HAc*2. A range, e.g. mol glycerol=1.8-2.2 mol HAc is also suitable. Sugar may optionally be added together with the glycerol. The sugar may be any sugar, e.g glucose, xylose and/or arabinose, as such or as part of any substrate e.g. lignocellulose hydrolysate and/or a fraction of lignocellulose hydrolysate.

In an embodiment, the pH of the mixture in the fed batch reactor in the fed batch mode is kept substantially constant by addition of sufficient lignocellulosic hydrolysate. In an embodiment, the concentration of acetic acid in the fed batch reactor is 30 g/l or less. In an embodiment, the rate of lignocellulosic hydrolysate fed into the fed batch reactor is 0,10 h$^{-1}$ or less. In an embodiment, the rate of lignocellulosic hydrolysate fed into the fed batch reactor is from 0.01 h$^{-1}$ to 0.10 h$^{-1}$. In an embodiment, the pH in the reactor in fed batch mode is pH 4 to pH 7, preferably pH 4 to pH 5. In an embodiment, the yeast can anaerobically ferment at least one C6 sugar and at least one C5 sugar.

d) After sufficient fermentation time, isolation of fermentation product from the reactor is conducted. Sufficient fermentation time is time when a desired amount of fermentation product is formed. This depends, amongst other, on the microorganism used, the pitch of the microorganism, and the carbon source. For example a suitable fermentation time may be e.g. about 72 hours, about 60 hours, about 48 hours or about 24 hours.

e) optionally keeping the remaining fraction after isolation of step d) as spent broth; and This step can be executed with known techniques (e.g. separation and storing techniques).

f) optionally using the spent broth in step a) to dilute the carbon source.

It is a unique feature of the spent broth i.e. the fermented broth from a fermentation process using HAc-converting strains in combination with a feeding strategy as described here, that it has a significantly reduced HAc content (compared to the un-fermented hydrolysate). This allows (part of) the spent broth or distilled fermentation broth (stillage) to be recycled into the batch-phases of subsequent propagation and fermentation cycles without introducing inhibitory concentrations of HAc.

If this spent broth also contains residual glycerol, this will be recycled in the fraction that is applied in a subsequent fermentation cycle, lowering the required glycerol supplementation of the hydrolysate, thereby improving the economics of the conversion process.

The invention thus includes recycling of part of the fermented broth, with decreased HAc-content and containing residual glycerol, into the batch phase of a subsequent propagation or fermentation cycle.

The invention further relates to a fermentation product obtained according to the process described herein above. In an embodiment, the fermentation product is ethanol. In an embodiment, to the fermentation process a propagation process is added. In an embodiment, is the process or processes are continuous.

Lignocellulosic Hydrolysate

Lignocellulosic hydrolysate is herein any hydrolysed lignocellulose. Lignocelllulose is herein biomass. It herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

The lignocellulosic hydrolysate may be acidic. In an embodiment, the lignocellulosic hydrolysate comprises organic acid. Examples of organic acids possible in lignocellulosic hydrolysate are acetic acid and formic acid. In an embodiment the organic acid is acetic acid. Acidic lignocellulosic hydrolysate is common product from pretreatment wherein acid is used, which results in formation of acetic acid.

The Cell

The cell used in the invention is capable of converting sugar, glycerol and acetic acid.

In an embodiment, is capable of producing fermentation product e.g. ethanol from acetic acid and glycerol while having also abilities of fermenting hexoses (glucose, fructose, galactose, etc) as well as pentoses like xylose and arabinose.

In an embodiment the cell is a yeast cell. Example of suitable yeast cells are yeast cells that are genetically modified comprising:

a) one or more nucleotide sequence encoding a heterologous NAD+-dependent acetylating acetaldehyde dehydrogenase (E.C. 1.2.1.10);

b) one or more nucleotide sequence encoding a homologous or heterologous acetyl-CoA synthetase (E.C. 6.2.1.1);

c) one or more nucleotide sequence encoding a heterologous glycerol dehydrogenase (E.C. 1.1.1.6); and d) one or more nucleotide sequence encoding a homologous or heterologous dihydroxyacetone kinase (E.C. 2.7.1.28 or E.C. 2.7.1.29).

In an embodiment, the cell has a deletion or disruption of one or more endogenous nucleotide sequence encoding a glycerol 3-phosphate phosphohydrolase and/or encoding a glycerol 3-phosphate dehydrogenase gene. Such cells are e.g. described in European Patent Application EP13182222.3, the contents of which is incorporated herein.

In an embodiment, the yeast cell has a deletion or disruption of one or more endogenous nucleotide sequence encoding a glycerol 3-phosphate phosphohydrolase and/or encoding a glycerol 3-phosphate dehydrogenase gene. In an embodiment, during the process no base needs to be added to the mixture in the reactor.

In an embodiment, the yeast is capable of metabolizing organic acid, preferably of metabolizing acetic acid. In an embodiment the cell has one or more nucleotide sequence encoding a glycerol transporter. Such cells are described in European Patent Application EP13182225.6, the contents of which is incorporated herein, e.g. a glycerol transporter from *Zygosaccharomyces rouxii* (ZYRO0E01210p).

In one embodiment the cell is able to ferment C5 and/or C6 sugar e.g. xylose, arabinose, mannose or galactose. In an embodiment of the invention the transformed host cell comprises one or more of: a xy/A-gene, XYL1 gene and XYL2 gene and/or XKS1-gene, to allow the transformed host cell to ferment xylose; and one or more, or two to ten copies of araA, araB and araD, genes, wherein these genes may be integrated into the cell genome, to allow the cell to ferment arabinose; deletion of the aldose reductase (GRE3) gene; overexpression of PPP-genes TAL1, TKL1, RPE1 and RKl1 to allow the increase of the flux through the pentose phosphate pathway in the cell.

In an embodiment, the transformed host cell is an industrial cell, more preferably an industrial yeast. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these to changes in environmental conditions which may occur in the applications they are used, such as in the baking industry, brewing industry, wine making and the ethanol industry. In one embodiment, the industrial transformed host cell is constructed on the basis of an industrial host cell, wherein the construction is conducted as described hereinafter. Examples of industrial yeast (*S. cerevisiae*) are Ethanol Red® (Fermentis) Fermiol® (DSM) and Thermosacc® (Lallemand).

In an embodiment the transformed host cell is inhibitor tolerant. Inhibitor tolerance is resistance to inhibiting compounds.

Acetic Acid

Acetic acid is herein understood to include equivalent acetate. Acetic acid i.e. acetic acid/acetate and also formic acid/formate form part of hydrolysed lignocellulosic material, that may be used in the invention as carbon source. Lignocellulosic hydrolysates contain high amounts of acetic acid, which is a potent inhibitor of the fermentative capacity of microorganisms, such as yeasts. Therefore in a process according to the invention inhibition of the cell by acetic acid is avoided. The process may be conducted according to the following embodiments.

An anaerobic or anoxic fed-batch fermentation process in which the pH of the fermentation broth in the reactor is higher than the pH of the feed (for the fed batch). In an embodiment the feed of acetic acid is lower than the conversion rate of acetic acid by the cell.

In an embodiment, the fed-batch fermentation process is conducted while the concentration of acetic acid in the fermentation medium is 3-15 g/l HAc. In an embodiment the pH of the fermentation broth in the reactor is ≤5 and ≥3.5, e.g. pH 4-4.5.

In an embodiment the in the fed-batch fermentation process substrate concentrations (C6 and C5 sugars, glycerol and HAc) are kept low, e.g. 10 g/l or less, 7 g/l or less, 5 g/l or less or 2 g/l or less.

The Fed-Batch Process

The fed-batch process may be a fermentation process, i.e. a process which leads to a fermentation product or a propagation process, where cells are the product. In an embodiment thereof, the process is a combined continuous propagation & fermentation process.

In an embodiment a propagation process is an aerobic carbon-limited and/or pH-regulated fed-batch propagation. HAc-conversion is the rate-limiting step in such a process.

Advantages of the fed-batch include:

Acetic acid (HAc), but also other substrate concentrations (C6 and C5 sugars, glycerol) are all kept low during the fermentation, removing/reducing their respective growth-inhibiting effects (decoupling, osmotic etc.). As compared to a batch fermentation or a traditional sugar-limited fed-batch fermentation this results in:

fermentation of hydrolysates in which the effects of HAc on the yeast's growth and survival are so severe that they result in insufficient biocatalyst activity to complete substrate conversions is enabled.

Reduced yeast pitch requirement in hydrolysates with less severe inhibitor content.

Reducing the risk of, and actual sugar losses to bacterial contaminants in the fermentation by:

Enabling fermentation of HAc-containing lignocellulosic hydrolysates at a lower pH than the pH 5-5.5 common for fermentations of lignocellulosic hydrolysate. Fermentation can now even take place at pH below pKa of HAc;

EtOH concentration is higher throughout the fermentation compared to a sugar-limited or non-sugar limited fed-batch fermentation, and even more so compared to a batch fermentation;

These effects also decrease/remove the requirement for addition of antibiotics.

The process results in lower requirement for titrant after enzymatic hydrolysis and before fermentation, costs savings of 0.01-0.02 $/gal EtOH produced (compared to a 17% dm corn-stover hydrolysate pH adjusted with ammonia before fermentation).

The invention is illustrated by the following examples, that should not be interpreted as to limit the scope of the invention.

EXAMPLES

Materials and Methods
Media

Strains were pre-cultured on solid medium containing 10 g/l yeast extract, 20 g/l phytone, 20 g/l glucose and 15 g/l agar (YPhD), and in liquid mineral medium (Luttik et al., 2000) set to pH 6.0 with 6N KOH and containing 200 mg/l histidine.

Fermentation experiments were performed using either synthetic mineral media (Luttik et al. 2000) or (NREL) pretreated corn stover hydrolysate. Whenever a strain was applied in a particular fermentation experiment that was auxotrophic for histidine, the fermentation medium was supplemented with this amino acid to a final concentration of 200 mg/l. Initial pH and concentrations of sugars, acetic acid and glycerol are listed separately in the experiment descriptions.

For fermentations of pretreated corn stover hydrolysate, 2 different batches were used. Both of these were derived from dilute acid pretreated corn stover separately obtained from NREL, and enzymatically hydrolyzed using DSM's proprietary enzyme cocktail after adjusting the pH of the pretreated material was adjusted (from approximately 1-2) to pH 4.5 using 2M ammonia. Compositions of these hydrolysates are given in table 1.

TABLE 1

Composition of the NREL dilute-acid-pretreated, enzymatically hydrolyzed corn stover hydrolysates

| Compound | Batch 1 (g/l) | Batch 2 (g/l) |
|---|---|---|
| Sugar monomers: | | |
| Glucose | 63.0$^a$ | 64.5$^b$ |
| Xylose | 40.9$^a$ | 33.6$^b$ |
| Arabinose | 4.8$^a$ | 4.1$^b$ |
| Mannose | 1.1$^a$ | |
| Galactose | 2.5$^a$ | |
| Fructose | 0.1$^a$ | |
| Inhibitors and byproducts: | | |
| Acetic acid$^b$ | 5.1 | 5.1 |
| Lactic acid$^b$ | ND | ND |
| Formic acid$^b$ | 0.3 | 0.2 |
| Glycerol$^b$ | ND | 0.4 |
| Ethanol$^b$ | ND | ND |
| Hydroxymethylfurfural (HMF)$^b$ | 0.2 | 0.4 |
| Furfural$^b$ | 1.0 | 0.7 |
| Other analyses: | | |
| pH | 4.2 | 4.3 |
| Dry Matter (% (m/m)) | 17.3 | 19.5 |
| Density | 1.06 g/ml | 1.05 g/ml |

$^a$Determined by HPAEC analysis,
$^b$determined by HPLC-H analysis,
ND = Not Detected, none or negligible amounts present.

Suspended solids in the hydrolysates were removed by centrifugation (30 min 4520×g) followed by filtration (106 μm) of the supernatant prior to fermentation. This was done to allow monitoring of yeast growth by OD measurement, and to simplify feeding of hydrolysate in fed-batch fermentations at lab scale.

Unless stated otherwise, ammonia (25% (w/v)) was added to adjust pH to 5,5 and also served as nitrogen source. To prevent outgrowth of any bacterial contaminants present in the hydrolysates, neomycin and penicillin G were added to a final concentration of 50 μg/ml and 100 μg/ml respectively. Approximately 250 μl of silicone antifoam (Dow Corning 1520) was added to each of the hydrolysates to prevent foaming.

Where mentioned, one of 2 industrial byproduct streams, abundantly available in bulk quantities, was added as a source of glycerol; being either 'syrup' or 'crude glycerin'.

Syrup (sometimes also referred to as 'solubles') is the concentrated liquid fraction of stillage (by evaporation), obtained from a traditional (1$^{st}$ generation) corn-starch-to-EtOH plant. 'Crude glycerin' is obtained from transesterification-based biodiesel production plant. Compositions of these glycerol sources are given in table 2.

TABLE 2

Composition of industrial glycerol sources 'syrup' and 'crude glycerin'

| Compound | Syrup (g/l) | Crude glycerin (g/l) |
|---|---|---|
| Sugar monomers: | | |
| Glucose | a | b |
| Xylose | a | b |
| Arabinose | a | b |
| Inhibitors and byproducts: | | |
| Acetic acid[b] | 1.9 | |
| Lactic acid[b] | 20.9 | |
| Formic acid[b] | ND | |
| Glycerol[b] | 106.9 | |
| Ethanol[b] | ND | |
| Hydroxymethylfurfural (HMF)[b] | ND | |
| Furfural[b] | ND | |
| Other analyses: | | |
| pH | | |
| Dry Matter | % | |
| Density | g/ml | g/ml |

[a]Determined by HPAEC analysis,
[b]determined by HPLC-H analysis,
ND = Not Detected, none or negligible amounts present.

Strains

The strains used in the experiments were YD01248, YD01397 and YD01437, which were derived from RN1001, RN1041 and RN1069 subsequently, as described below.

Strain RN1001 is the parent strain of strain RN1041, i.e. before deletion of the HIS3-gene.

RN1041 has been described in WO 2012/067510. This strain has the following to genotype: MAT a, ura3-52, leu2-112, his3::loxP, gre3::loxP, loxP-pTPl1::TAL1 , loxPpTPl1::RKl1 , loxP-pTPl1-TKL1 , loxP-pTPl1-RPE1, delta::pADH1-XKS1-tCYC1-LEU2, delta::URA3-pTPl1-xylA-tCYC1 MAT a=mating type a ura3-52, leu2-112, HIS3::loxP mutations in the URA3, LEU2 and HIS3 genes respectively. The ura3-52 mutation is complemented by the URA3 gene on the Piromyces xylA overexpression construct; the leu2-112 mutation is complemented by the LEU2 gene on the XKS1 overexpression construct. The deletion of the HIS3-gene causes a histidine auxotrophy. For this reason, RN1041 needs histidine in the medium for growth.

gre3::loxP is a deletion of the GRE3 gene, encoding aldose reductase. The loxP site is left behind in the genome after marker removal.

loxP-pTPl1 designates the overexpression of genes of, in the experiments described herein, the non-oxidative pentose phosphate pathway by replacement of the native promoter by the promoter of the TPl1 gene. The loxP site upstream of the strong, constitutive TPl1 promoter remains in the genome after marker removal (Kuyper et al, FEMS Yeast Research 5 (2005) 925-934).

delta:: means chromosomal integration of the construct after recombination on the long terminal repeats of the Ty1 retrotransposon.

Strain RN1069 is derived from RN1041: the GPD1 and GPD2 genes were disrupted by gene replacement. The construction of strain RN1069 is also described in detail in WO2013/081456. The genotype of strain RN1069 is: MAT a, ura3-52, leu2-112, his3::loxP, gre3::loxP, loxP-pTPl1::TAL1 , loxP-pTPl1::RKl1 , loxP-pTPl1-TKL1 , loxP-pTPl1-RPE1, delta::pADH1-XKS1-tCYC1-LEU2, delta::URA3-pTPl1-xylA-tCYC1 gpd1::hphMX, gpd2::natMX. Due to an unknown reason, this strain has lost its natMX-marker, i.e. it is no longer resistant to nourseothricin. This allowed for the use of this marker in subsequent transformation experiments. However, also another marker could have been used instead.

Strain YD01248 has been described in WO2015028583, see e.g. examples 2 and 3.

TABLE 3

Expressed glycerol/acetic acid genes, encoding desired enzyme activities in strain YD01248.

| Gene | Source organism | Enzyme activity |
|---|---|---|
| acdH | Lactobacillus plantarum | Acetaldehyde dehydrogenase |
| ACS2 | Saccharomyces cerevisiae | Acetyl-CoA ligase |
| gldA | Escherichia coli | Glycerol dehydrogenase |
| DAK1 | Saccharomyces cerevisiae | Dihydroxyacetone kinase |

Strain YD01437 has been derived from strain YD01248 through removal of selection markers, and introduction of a putative glycerol transporter from Zygosaccharomyces and is described in detail in WO2015028583 , in particular in examples 6 and 7, strain T5.

Preculture preparation

A loopfull of frozen (glycerol) stock culture was streaked on YPhD (see 'Media') and incubated for 3 days at 30 ° C. Obtained yeast biomass was transferred from the agar plate to a 500 ml shake flask containing 200 ml of a mineral medium (Luttik et al., 2000) that had been set to pH 6.0 with 6N KOH and contained 200 mg/l histidine. Cultures were incubated overnight (17-20hrs) in a shaker incubator (200 RPM) at 32° C. Cells were harvested by centrifugation (3 min, 13500×g) and washed with 50 ml cold (4° C.) sterile demineralized water. Cell pellets were suspended in ⅓ of the original culture volume of cold (4° C.) sterile demineralized water. Fermentation inoculum volume was calculated from the OD700 of the suspension using a previously determined linear correlation between OD700 and (dry) yeast biomass for the particular strain.

Batch-Fermentation Conditions

Unless stated otherwise, a volume of 400 ml fermentation medium in 500 ml flasks (80% filling) was used for each fermentation test, which was inoculated from a suspension of pre-cultured cells to a (dry) yeast biomass concentration of approximately 0,5 g/l. When strains with histidine-auxotrophy were used in the fermentation, histidine was added to the hydrolysate medium to a final concentration of 200 mg/l.

Batch-fermentation tests were performed using the Alcohol Fermentation Monitor (AFM) (Applikon Biotechnology, Schiedam, the Netherlands), with temperature controlled at 32° C. and stirred at 250 RPM. Broth pH was not controlled during fermentations. $CO_2$ production was measured online by the AFM, correlating with the sum of ethanol (EtOH) and biomass formation, and samples were taken periodically during the fermentation to determine yeast growth-, substrate utilization- and product formation.

Fed-Batch-Fermentation Conditions

Fed-batch fermentations were performed similar to batch-fermentation experiments.

At final volumes of 400-800 ml, the Biological Activity Monitor (BAM) (Halotec, Veenendaal, the Netherlands) was used; essentially a predecessor of the AFM instrument in which the fermentation flasks are stirred with regular magnetic stirrers and incubated at 32° C. using a water bath. Dosing of feed was performed using programmable HPLH pumps equipped with HPLH 20VS or HPLH 200VS pump heads (CAT, Staufen, Germany).

Fed-batch fermentations at final volumes of 800-2000 ml, as well as all other experiments where pH-was monitored, were performed using Minifors fermenters (Infors-HT, Basel, Switzerland).

Sample Analysis

Glucose, xylose, arabinose, ethanol, acetic acid and glycerol in the fermentation broth samples were quantified using a Shimadzu ('s-Hertogenbosch, The Netherlands) HPLC system with column oven CTO-10A-vp and Auto-injector SIL-10AD-vp equipped with a guard column (Bio-Rad H cartridge) and an Aminex HPX-87H column (300×7.8 mm; Bio-Rad, Hercules, USA). Elution took place at 80° C. with 5 mM $H_2SO4$ at 0.6 ml*$min^{-1}$. The eluate was monitored using a Refractive Index detector RID-10A (Shimadzu, 's-Hertogenbosch, the Netherlands).

Note that when using this separation column, xylose, fructose, mannose and galactose have similar retention times. Reported numbers for xylose marked with "analyzed using HPLC-H" therefore include all of these sugar monomers. As can be seen from table 1, xylose content of the applied hydrolysates is much higher than for these other sugar monomers, and these therefore have only a minor effect on reported xylose numbers.

Where mentioned, monosaccharide concentrations (glucose, xylose, arabinose, galactose, mannose, fructose) were analyzed separately by high-performance anion-exchange chromatography (HPAEC). HPAEC was performed on a Dionex (Sunnyvale, USA) ICS3000 system equipped with a Dionex CarboPac PA-1 column (4 mm ID×250 mm) in combination with a Dionex CarboPac PA guard column (4 mm×50 mm) and an ED50-detector (Dionex). Isocratic elution (20° C., 1 ml*$min^{-1}$) of 23 min was carried out with water. Each elution was followed by a washing—(2 min 0,15 M NaOH, 3 min 0,15 M NaOH+1 M NaAc, 1 min 0,15 M NaOH) and an equilibration step (1 min water).

Yeast biomass concentration in the fermentation broth samples was approximated by measuring the OD of the samples at 700 nm in a spectrophotometer (Perkin-Elmer Lambda 2), corrected for OD of fermentation medium, and calculated to (dry) yeast biomass using a previously determined (strain and instrument-specific) linear correlation factor. Broth samples were diluted to this linear range (generally between 0-1 OD units) when necessary.

Comparative Experiment A

Fermentation Characteristics of Strain YD01248

Strain YD01248 was applied in a fermentation on synthetic medium containing approximately 20 g/l glucose, 20 g/l xylose, 2 g/l acetic acid and 5 g/l glycerol. Initial pH of the medium was adjusted to 4,5 with 6M KOH. The fermentation medium was inoculated to an OD600 of approximately 0,9 (corresponding to approximately 0,15 g/l (as dry) yeast biomass). The results are given in FIG. 1. Fermentation behavior of YD01248 on synthetic medium; Sugar conversion and EtOH production (A), glycerol- and HAc conversion, biomass(B).

Figure 1B:
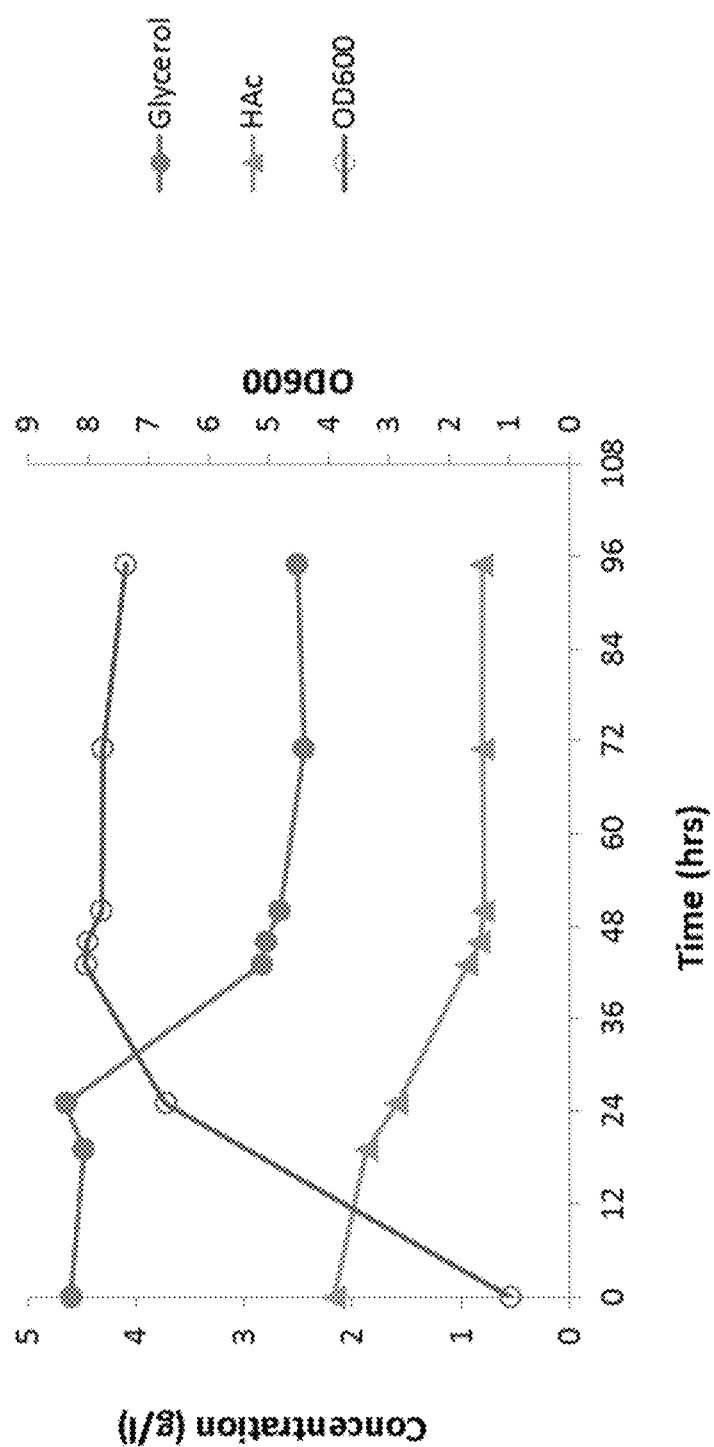

From FIG. 1 it can be inferred that during glucose fermentation, here until somewhat later than 24 hours, no significant glycerol conversion takes place. Only after glucose levels dropped below approximately 5 grams per liter, glycerol conversion commenced.

In the first 24 hours of the fermentation, acetic acid level dropped slightly (from 2.2 g/l to 1.6 g/l). Acetic acid conversion needs to take place during this phase in order to balance redox equivalents (re-oxidation NADH, generated during cellular growth, to $NAD^+$). However, after 24 hours, when glycerol conversion accelerated, also the rate of acetic acid conversion accelerated. Between 24 hours and 72 hours, more acetic acid is converted, due to glycerol conversion and some yeast growth (up to 48 hours).

However, although theoretically sufficient glycerol was present in the medium to supply the cells with enough NADH to convert all HAc to EtOH, 0,8 g/l HAc remained in the fermentation medium at the point when glycerol and HAc conversions stopped due to the depletion of xylose.

In order to improve glycerol import into the cells and thereby increase its degree of conversion, the concentration of externally provided glycerol was increased in the experiment described under Comparative experiment B.

Comparative Experiment B

Figure 2A:
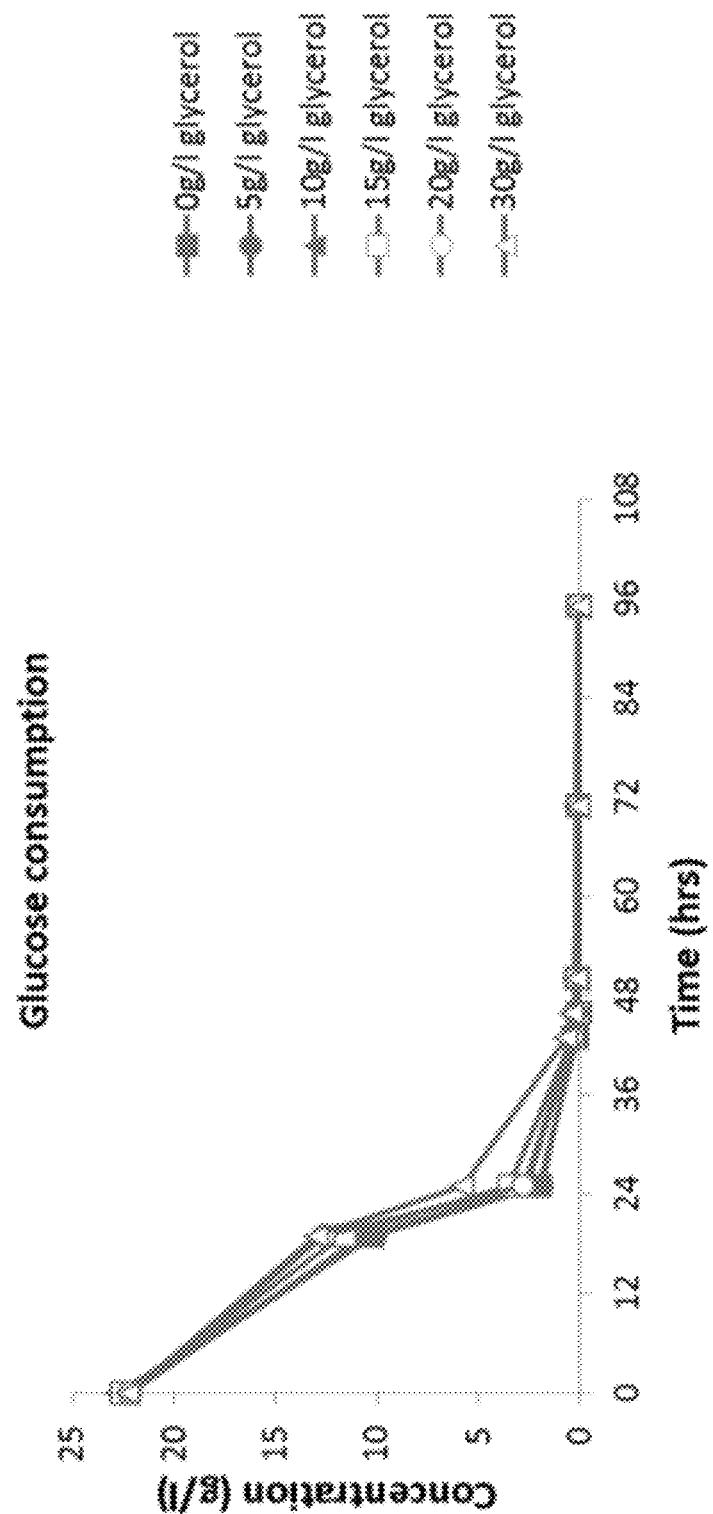
FIG. 2 Fermentation behavior of YD01248 on synthetic media at increasing glycerol concentrations.
Figure 2C:
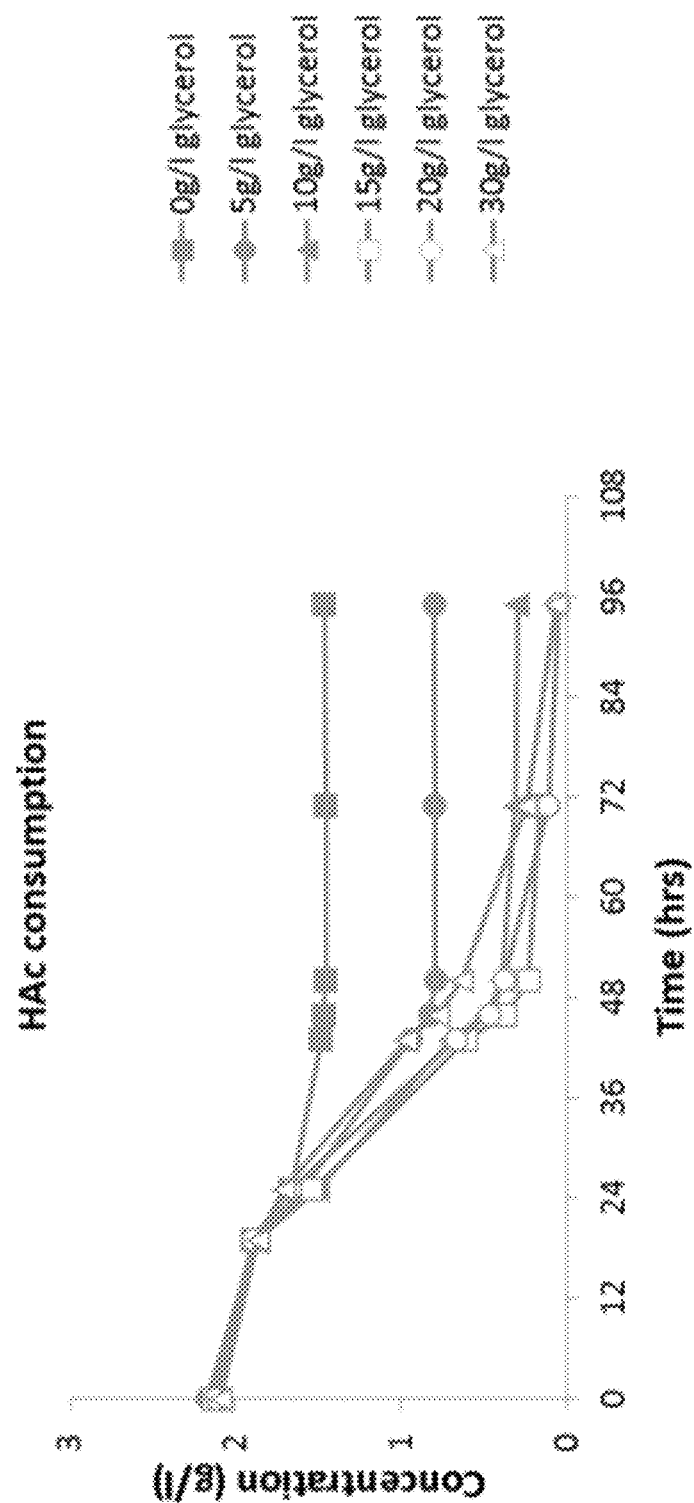
Figure 2D:
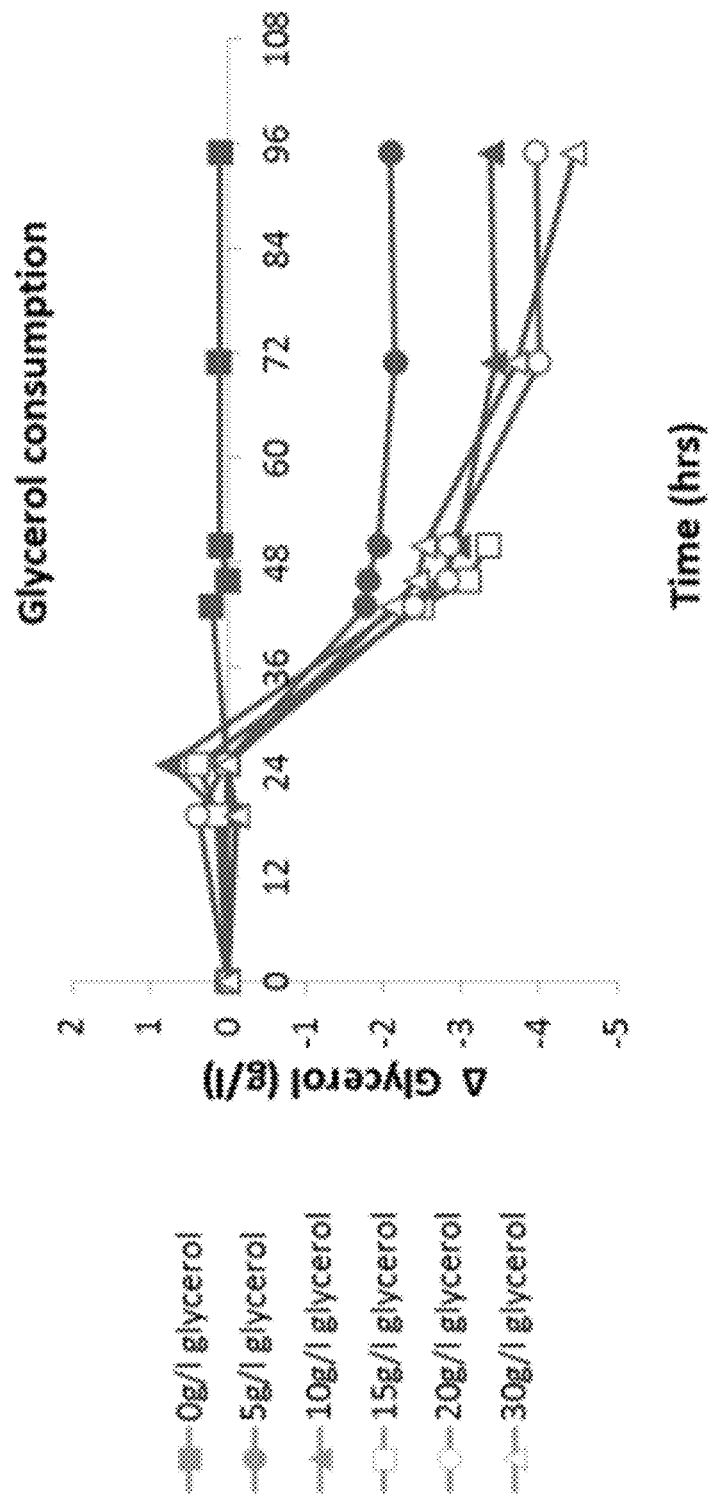
Figure 3A:
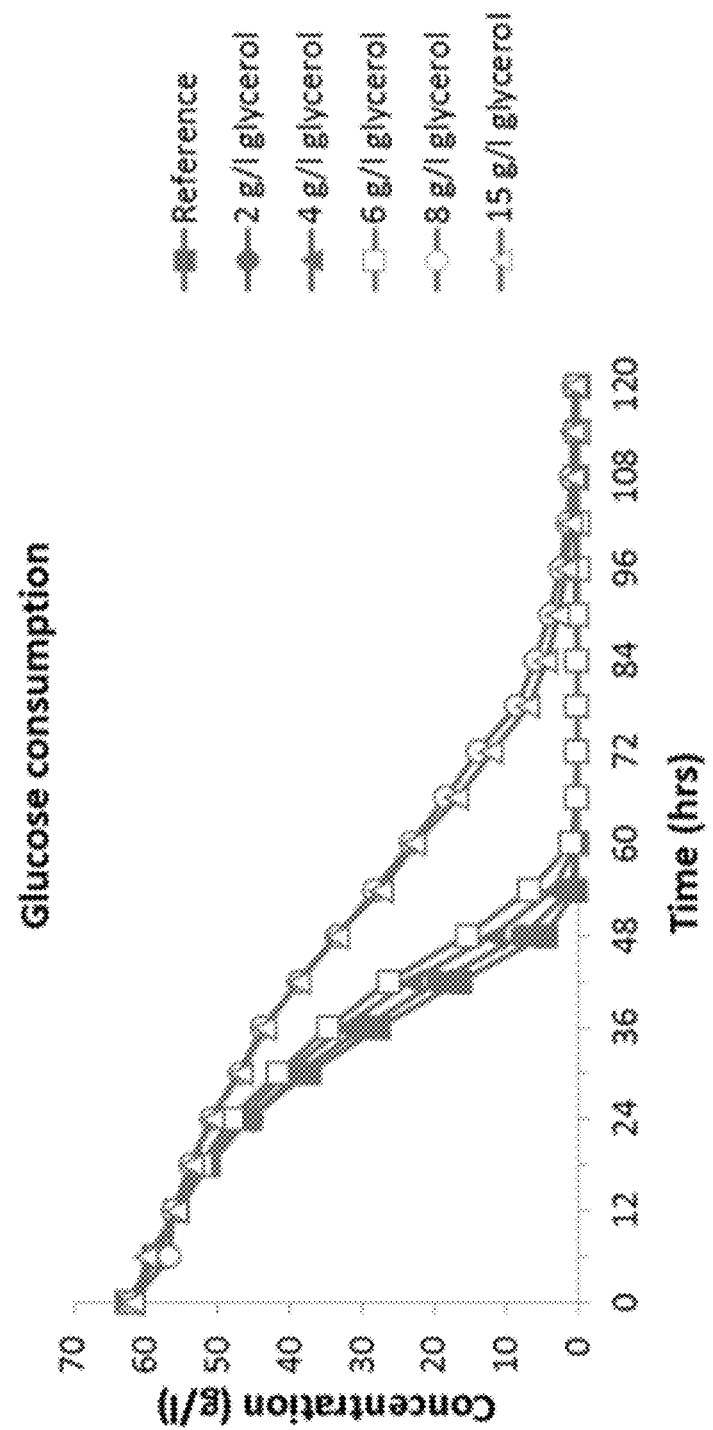
FIG. 3 Fermentation behavior of YD01248 on (NREL) pretreated corn stover hydrolysate supplemented with glycerol at different concentrations.
Figure 3B:
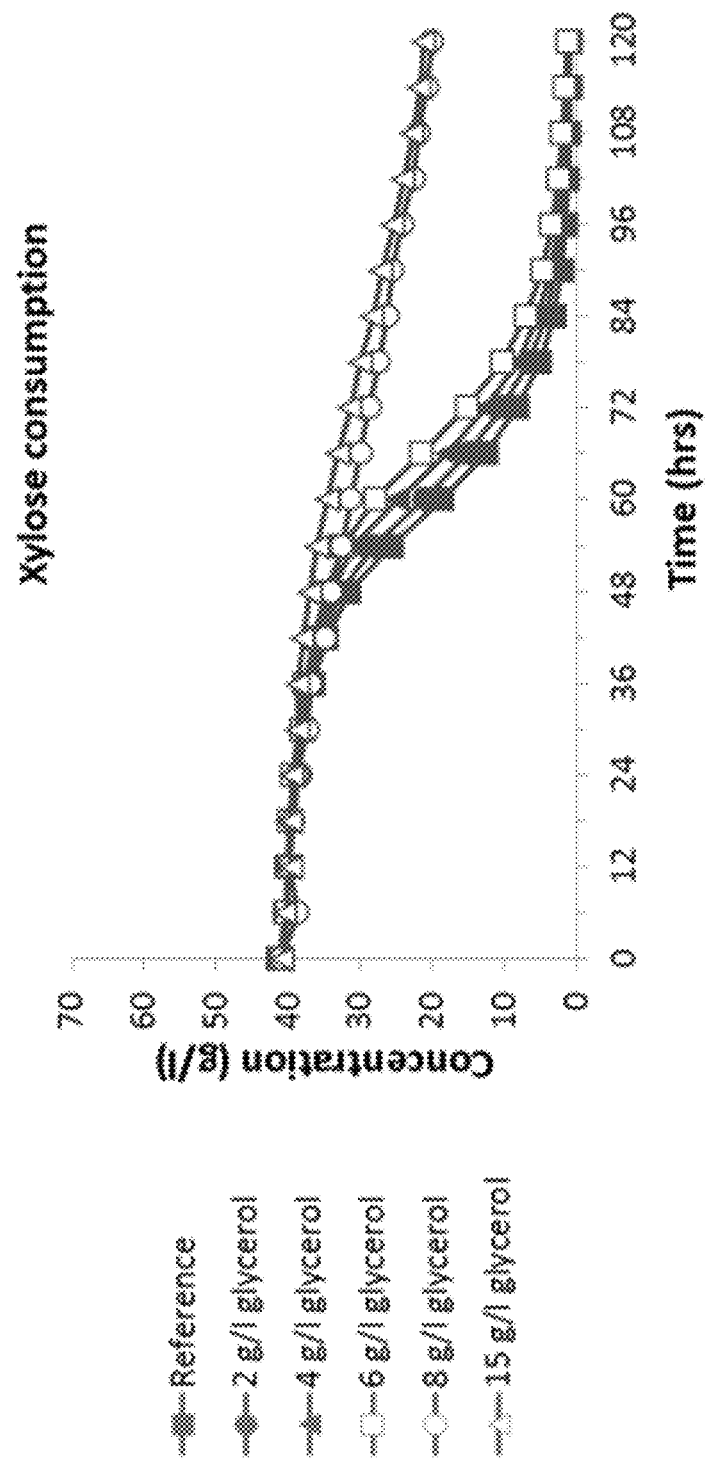
Figure 3C:
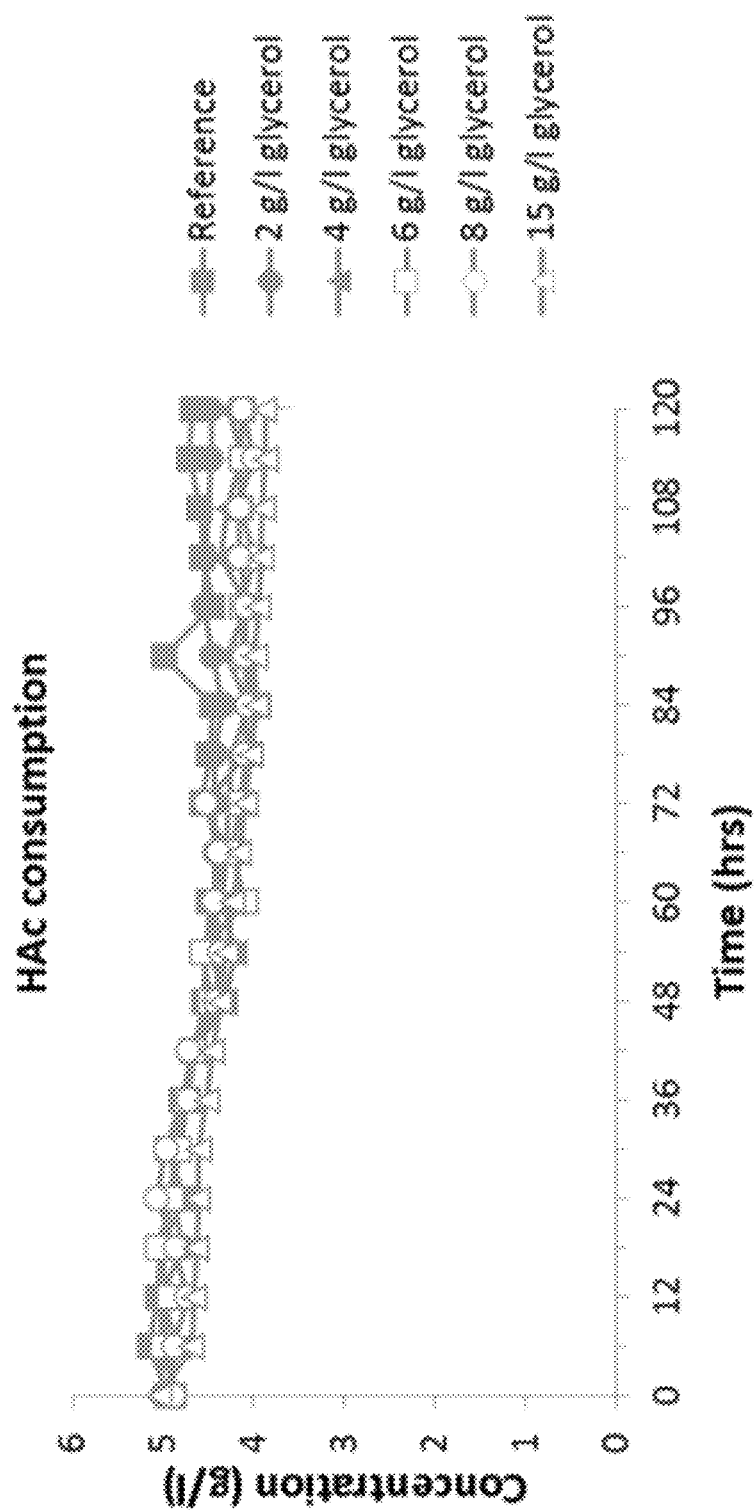
Figure 3D:
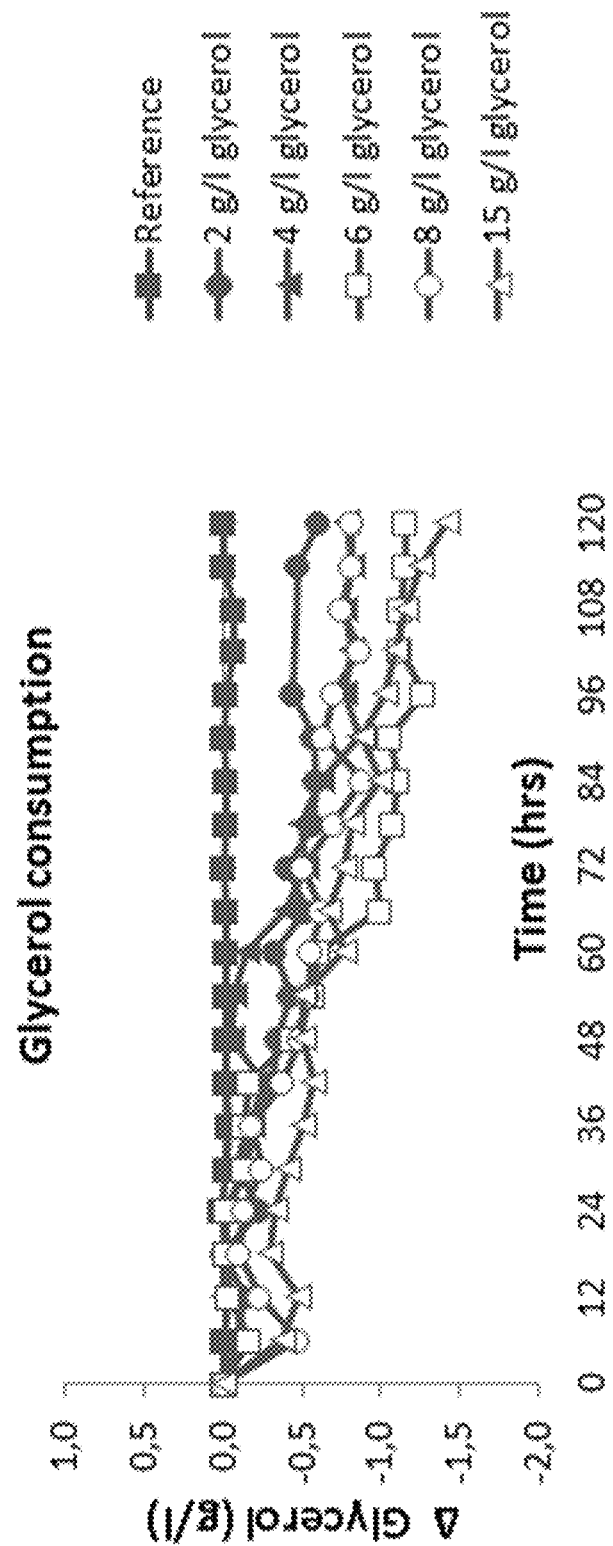

Fermentation Characteristics of Strain YD01248 in Synthetic Medium at Different Glycerol Concentrations Strain YD01248 was applied in fermentations on synthetic medium containing approximately 20 g/l glucose, 20 g/l xylose, 2 g/l acetic acid. Glycerol was added to the media at 0, 5, 10, 15, 20 and 30 g/l respectively. Initial pH of the medium was adjusted to 4,5 with 6M KOH. The fermentation media were inoculated to an OD600 of approximately 0,9 (corresponding to approximately 0,15 g/l (as dry) yeast biomass). The results are shown in FIG. 2. FIG. 2 shows that increasing the glycerol concentration from 5 g/l up to 30 g/l in the fermentation medium resulted in a higher degree of glycerol (2D) and HAc (2C) conversion. These increased glycerol concentrations however negatively influenced glucose (2A) and, to a larger extent, xylose conversion (2B).

Comparative Experiment C

Fermentation Characteristics of Strain YD01248 on Lignocellulosic Hydrolysate at Different Glycerol Concentrations Strain YD01248 was applied in fermentations on pretreated corn stover hydrolysate (NREL batch 1, see table 1) at 0,5 g/l (as dry) yeast biomass. Glycerol was added to the fermentation media at 0 (reference), 2, 4, 6, 8 and 15 g/l respectively. Initial pH of the medium was adjusted to 5,5 with 6M KOH.

Figure 4:
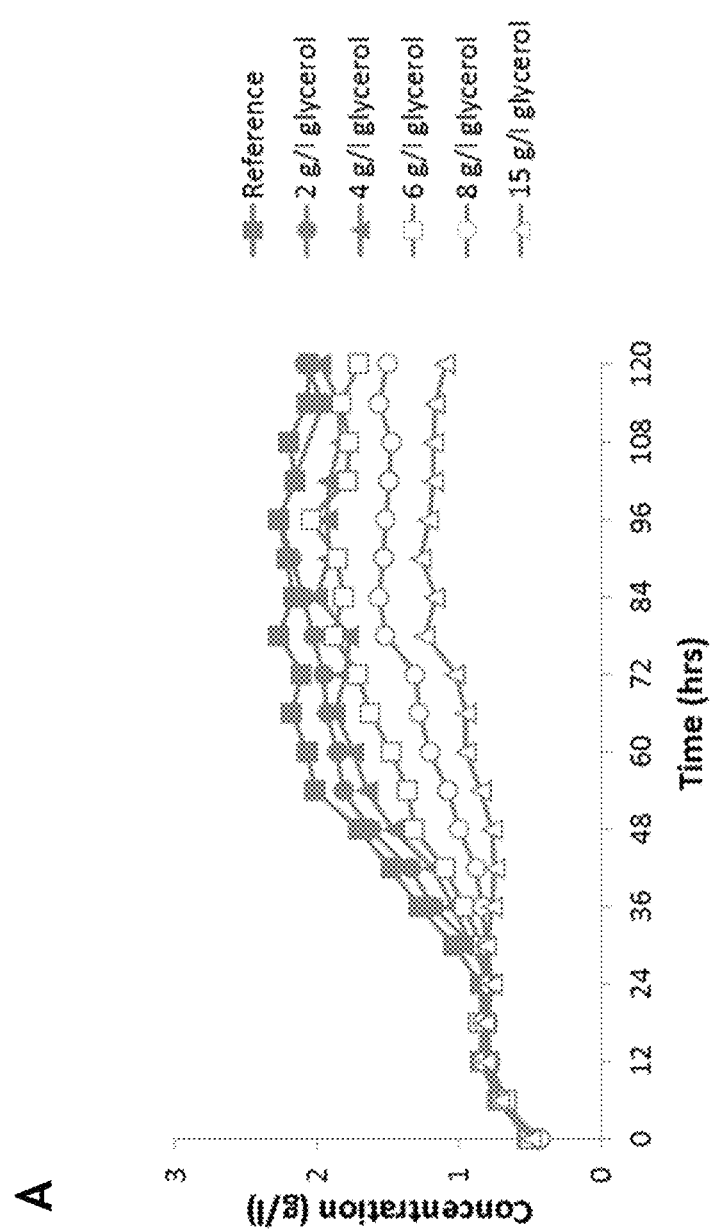
FIG. 4 Yeast biomass growth (calculated from OD700) (A), and conversion rates per biomass for glucose (B) and xylose (C) for YD01248 in fermentations of (NREL) pretreated corn stover hydrolysate supplemented with glycerol at different concentrations; the legend of FIGS. 4B and 4C is identical to that of FIG. 4A.
Figure 5A:
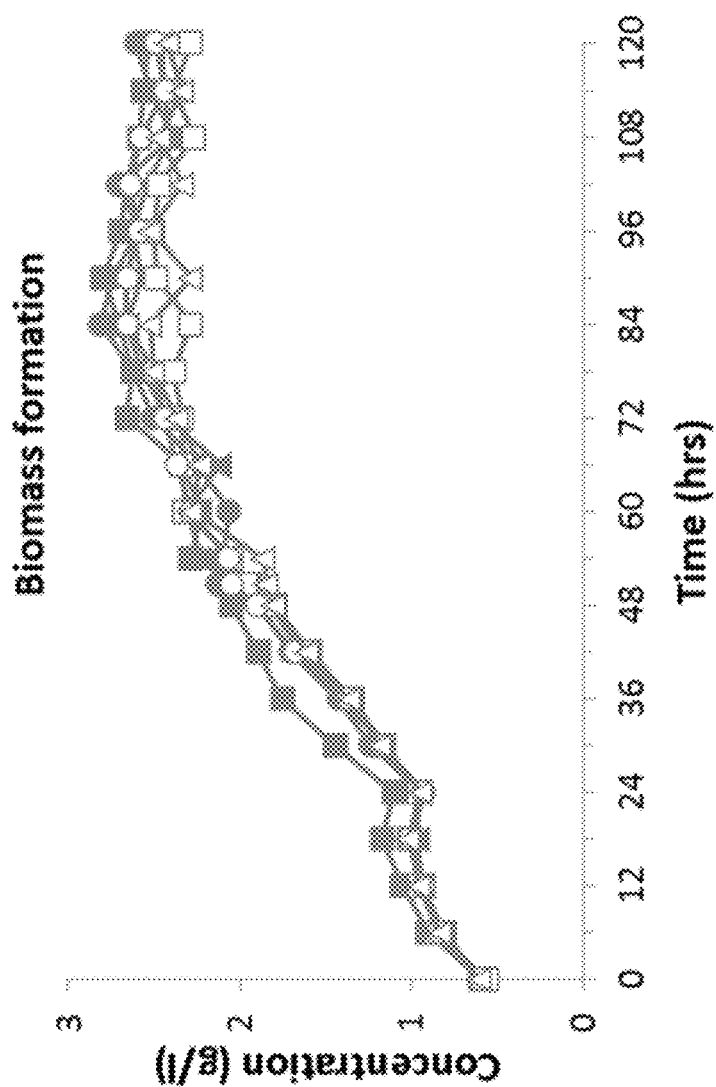
FIG. 5A Yeast biomass growth (calculated from OD700) (A) for YD01248 in fermentation of (NREL) pretreated corn stover hydrolysate supplemented with glycerol at different concentrations at the point of glucose depletion (50 hrs); the legend of FIGS. 5A, 5C and 5E is identical to that of FIG. 5B FIG. 5 B-E Yeast biomass growth (calculated from OD700) (A), glucose (B), xylose (C), HAc (D) and glycerol (E) conversion profiles for YD01248 in fermentation of (NREL) pretreated corn stover hydrolysate supplemented with glycerol at different concentrations at the point of glucose depletion (50 hrs)
Figure 5B:
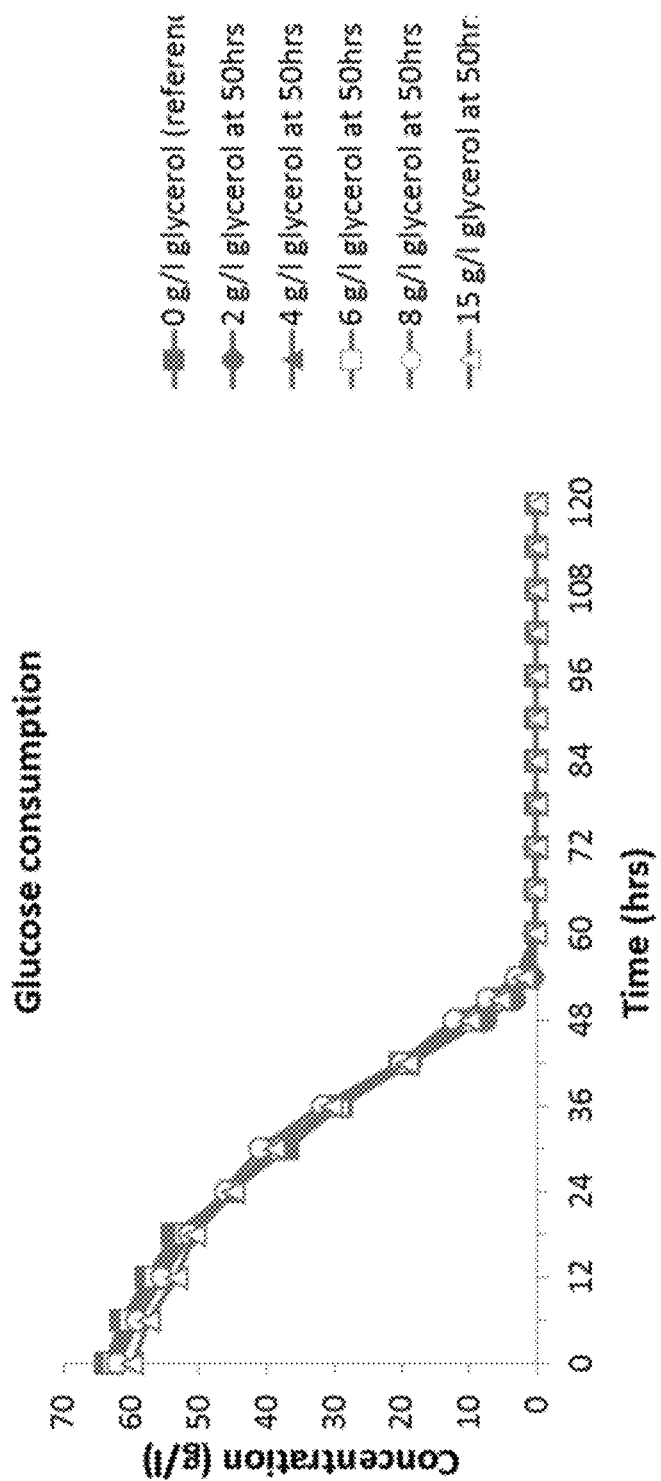
Figure 5C:
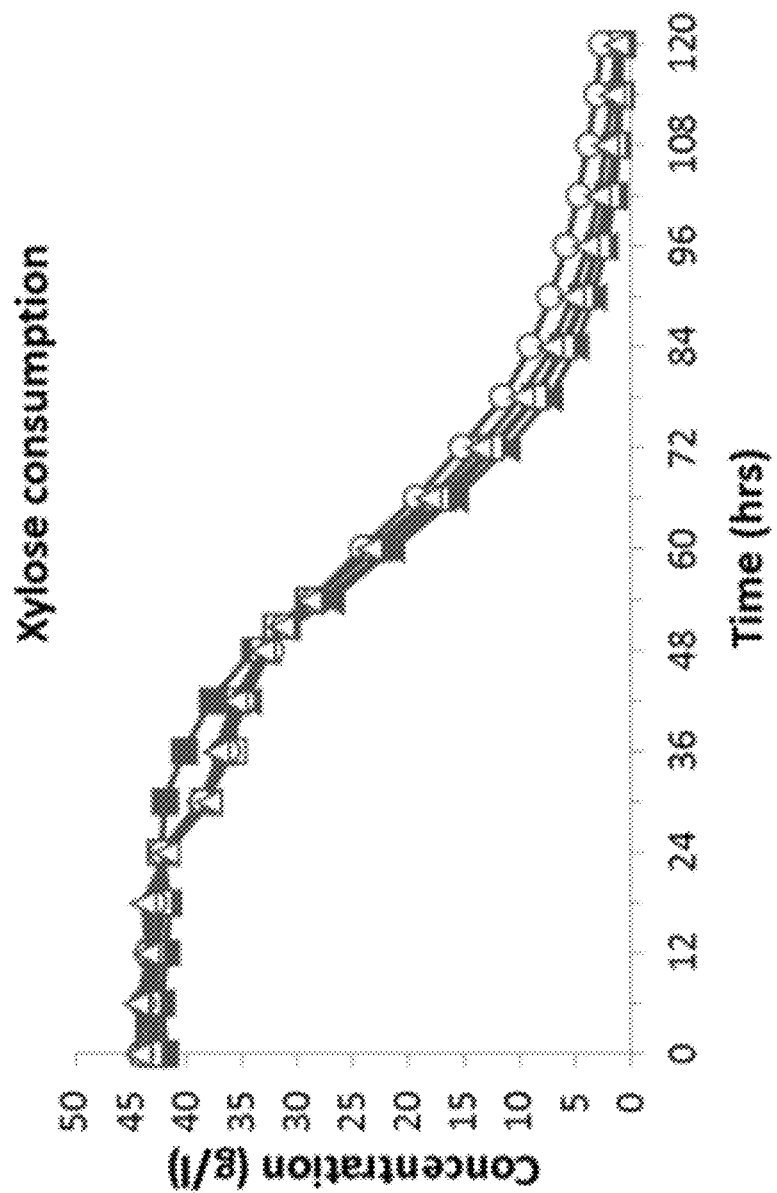
Figure 5D:
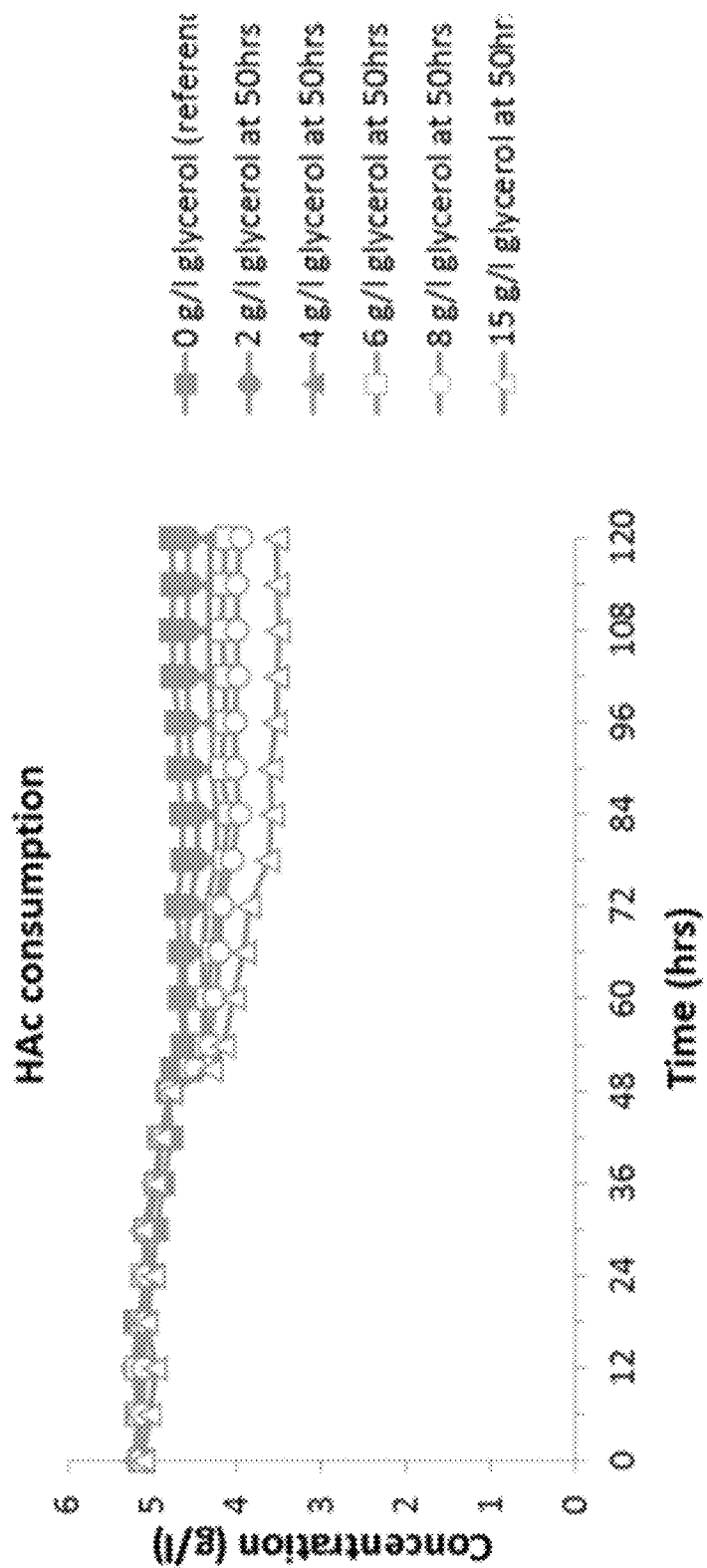
Figure 5E:
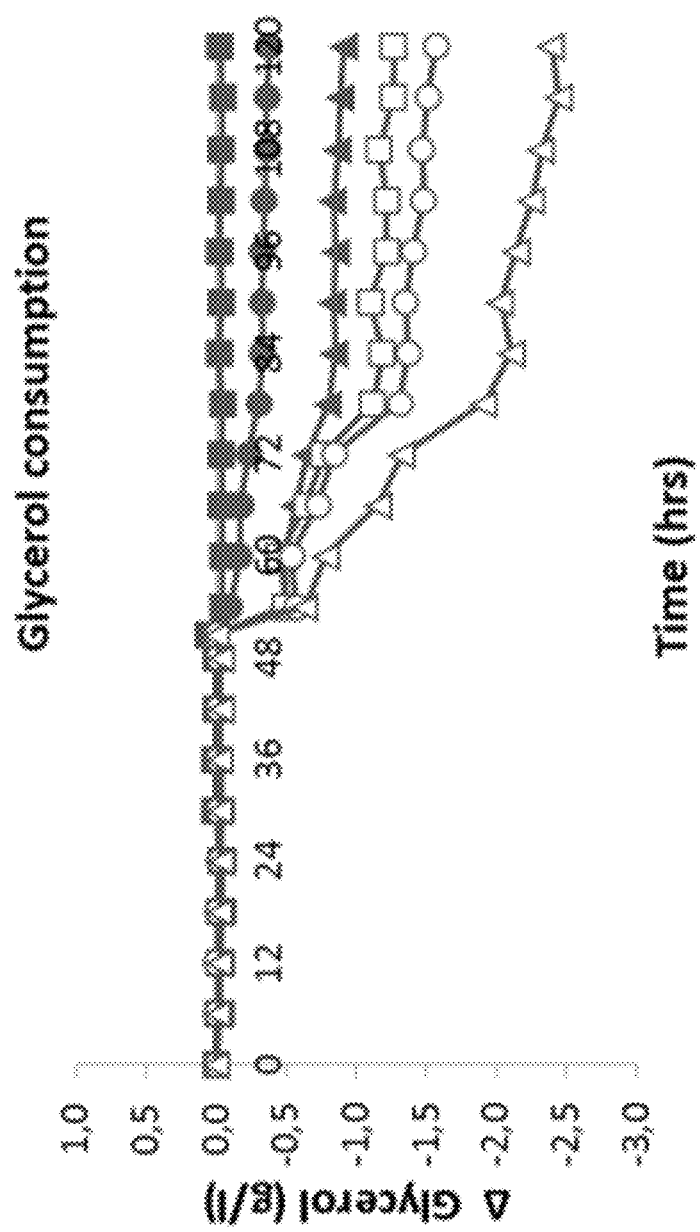
Figure 6A:
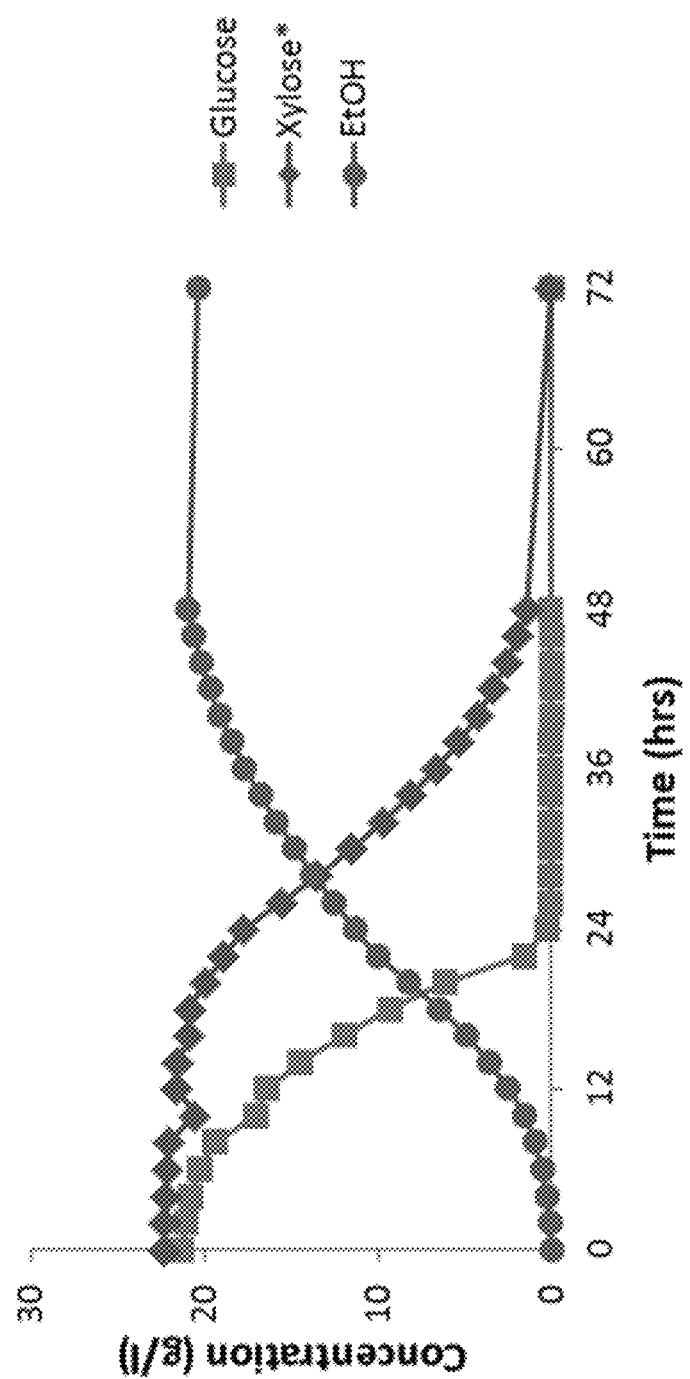
FIG. 6 Fermentation behavior of YD01397 (A,C) and YD01437 (B,D) on synthetic medium; Sugar conversion and EtOH production (A,B), glycerol- and HAc conversion, biomass (calculated from OD700) (C,D); the legend of FIG. 6B is identical to that of FIG. 6A; the legend of FIG. 6D is identical to that of FIG. 6C.
Figure 6B:
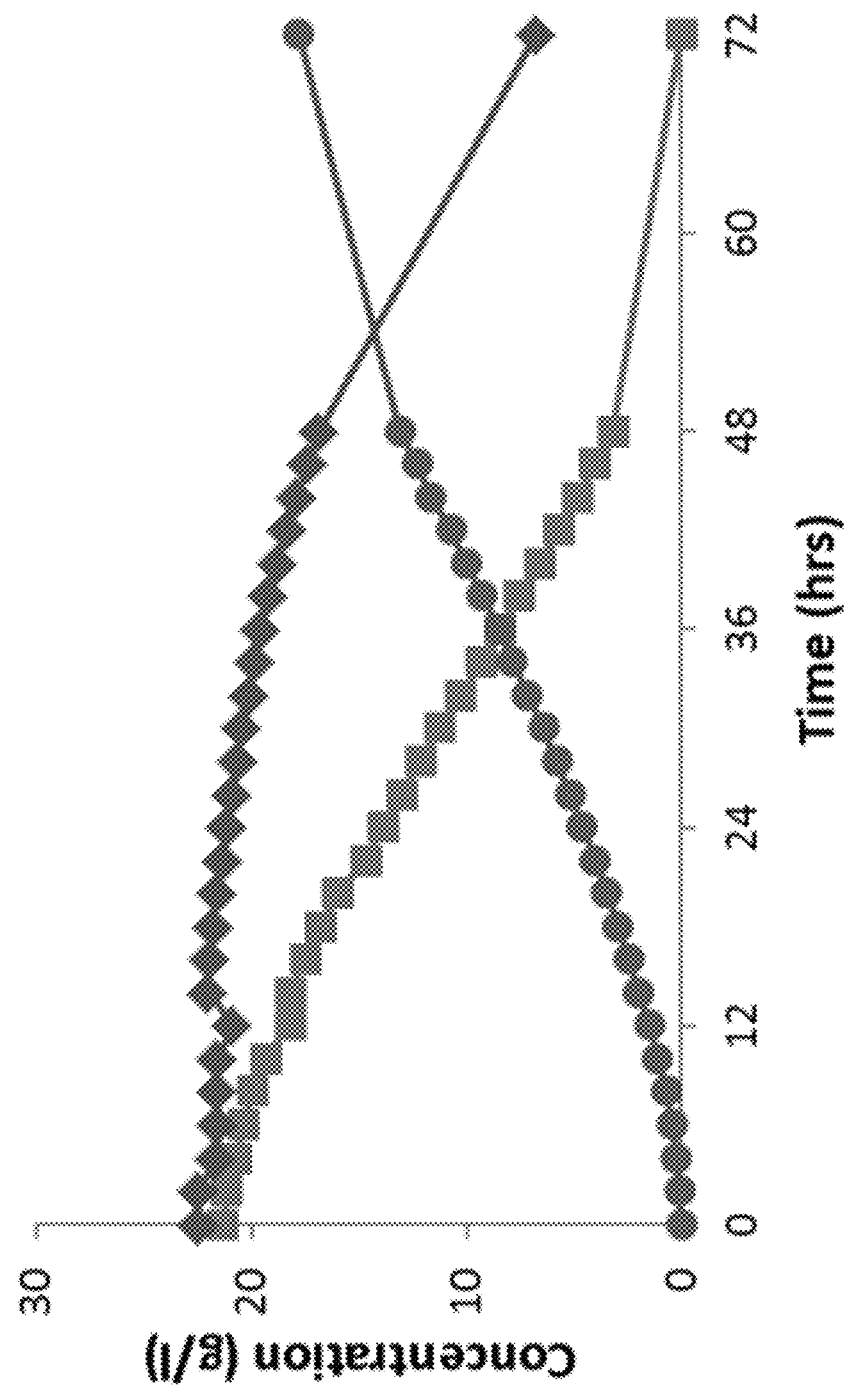
Figure 6C:
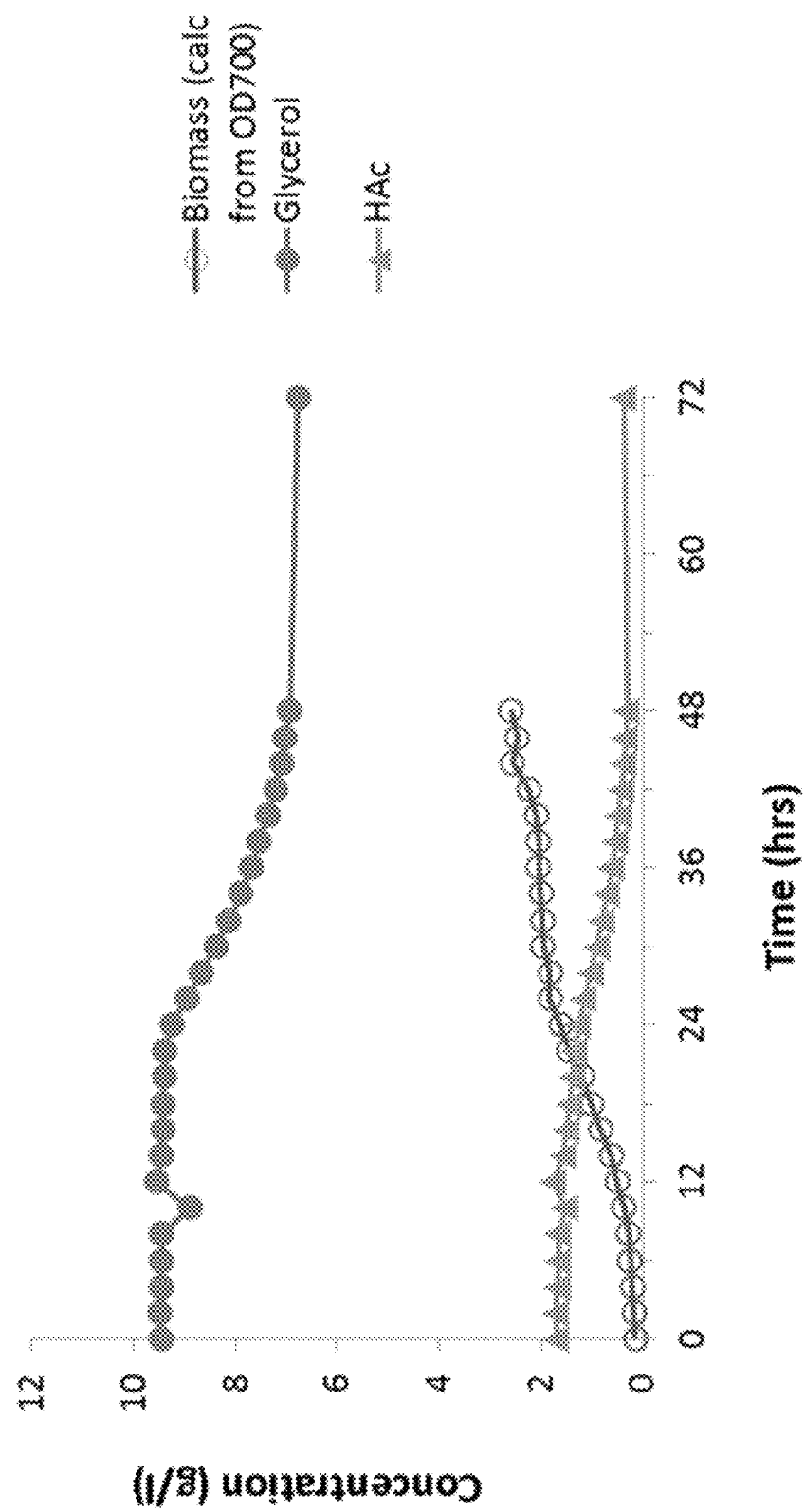
Figure 6D:
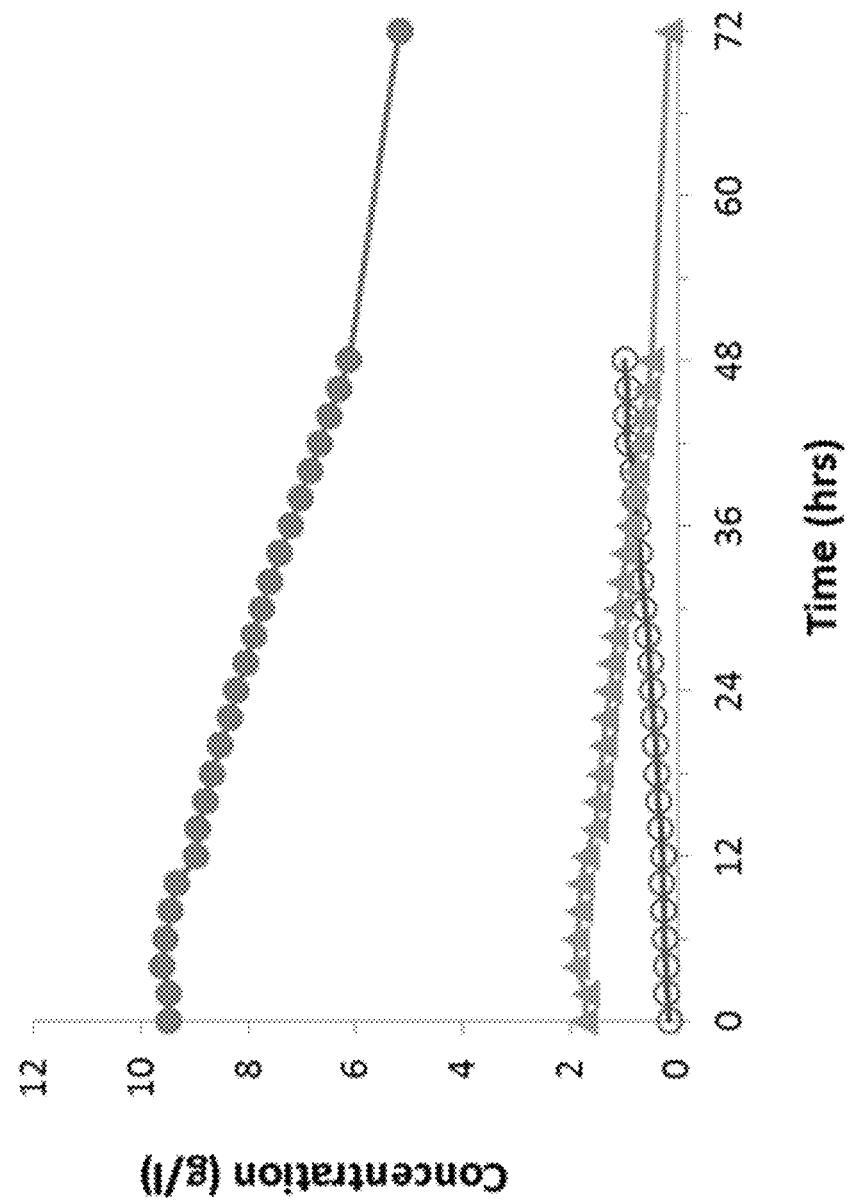

The results are shown in FIGS. 3 and 4. FIG. 3 shows that glycerol (3D) and HAc (3C) conversions were much lower in lignocellulosic hydrolysate than on synthetic medium (see Comparative experiment B). Whereas addition of glycerol at concentrations up to 6 g/l only negatively affected sugar conversion to a limited degree, there appears to be a sharp increase in its inhibiting effect at concentrations of 8 g/l and higher (3A,B), which would be required in order to allow complete conversion of the HAc present in the hydrolysate. As can be seen in FIG. 4, not only the growth rate of the yeast (A), and thereby the total amount of biocatalyst present in the fermentation, but also the glucose (B) and xylose (C) consumption rates per biomass are negatively affected by increasing concentrations of glycerol in the fermentation broth, both effects contributing to sub-optimal sugar conversion (rates).

These results indicate that when fermenting lignocellulosic hydrolysates supplemented with glycerol, using a glycerol- and HAc-converting strain comparable to YD01248, the optimum concentration of glycerol to be applied in the fermentation medium is a tradeoff between increased glycerol/HAc- and the degree of (C5) sugar conversion.

As glycerol is not utilized until glucose concentration becomes low, one way to improve this tradeoff would be to not provide the glycerol to the fermentation before its conversion would commence (at low glucose concentration). Thereby the negative effects of glycerol on the yeast's glucose conversion and growth rate are avoided without compromising glycerol conversion. In order to verify this assumption, the experiment described in comparative experiment D was performed.

Comparative Experiment D

Addition of Glycerol to Batch Fermentations of Lignocellulosic Hydrolysate at the End of Glucose Fermentation Strain YD01248 was applied in fermentations on pretreated corn stover hydrolysate (NREL batch 1, see table 1)) at 0,5 g/l (as dry) yeast biomass. Initial pH of the medium was adjusted to 5,5 with 6M KOH.

As glycerol is only converted after glucose drops below approximately 5 g/l (previous Comparative experiment C), it was added to concentrations of 0 (reference), 2, 4, 6, 8 and 15 g/l respectively, at the point when glucose was nearly depleted (50 hrs), in order to prevent inhibition of yeast growth in the glucose-fermentation phase.

FIG. 5 Shows that inhibition of yeast biomass formation was avoided when adding glycerol to the fermentation broth at the point where glucose was (nearly) depleted and the majority of growth has already occurred (5A). When applying this strategy, glycerol concentrations that proved to be strongly inhibitory of sugar conversions (≥8 g/l) in Comparative experiment C can be applied in order to improve glycerol (5D) and HAc (5E) conversions without compromising sugar conversion to a large extent, which leads to a more efficient ethanol production than if glycerol is added at the start of the fermentation. Maximum glycerol and HAc conversion achieved after 120 hrs of fermentation increased with 1.0 g/l (1.4 g/l to 2.4) and 0.4 g/l (from 1.2 g/l to 1.6 g/l) respectively.

When applying this method, the optimum glycerol concentration for glycerol and HAc conversion is ≥15 g/l. However, addition of glycerol to concentrations above the concentration theoretically required to fully convert the HAc present in a given hydrolysate (for this particular NREL-pretreated corn stover hydrolysate at 5.1 g/l HAc: 15.6 g/l glycerol at a stoichiometric conversion ratio of 2 moles glycerol per 1 mole of HAc (neglecting the HAc conversion enabled by NADH generated from anaerobic yeast growth)) would be sub-optimal from an economic perspective as it would inevitably leave relatively large amounts of glycerol unconverted.

A better solution to this problem would be to improve glycerol (and concomitantly HAc) conversion by extending the glycerol/HAc conversion window from only during the xylose fermentation phase to the full duration of the fermentation by enabling glucose-glycerol co-conversion. Expression of the glycerol-proton symporter from *Z. rouxii* in a glycerol and HAc-converting yeast strain (described in patent application WO2015028583 could allow for this, and should also improve affinity of the yeast to glycerol, offering the possibility of leaving less residual glycerol in the fermentation broth (comparative experiment E).

Comparative Experiment E

Batch Fermentations of Synthetic Media with Glycerol Using a Strain with Exogenous Glycerol Symporter.

Strains YD01397 (described in patent application WO2015028583, in particular in examples 6 and 7, strain T3) and YD01437 (expressing a glycerol-proton symporter from *Z. rouxii*, described in WO2015028583, in particular in examples 6 and 7, strain T5, were applied at approximately 0,125 g/l (as dry) yeast biomass in fermentations of synthetic medium containing approximately 20 g/l glucose, 20 g/l xylose, 2 g/l acetic acid and 10 g/l glycerol. Initial pH of the medium was adjusted to 4,5 with 6M KOH. The fermentation medium was inoculated to an OD600 of approximately 0,9.

FIG. 6 shows that where glycerol uptake in YD01397 only started after glucose had nearly been depleted (approximately 23 hrs), strain YD01437 clearly co-converted glucose and glycerol at 20 g/l glucose. Glycerol conversion rate (FIG. 7) was also dramatically increased in YD01437.

However, sugar conversion rate and biomass growth were severely inhibited by this increased level glycerol import and/or conversion.

Figure 7:
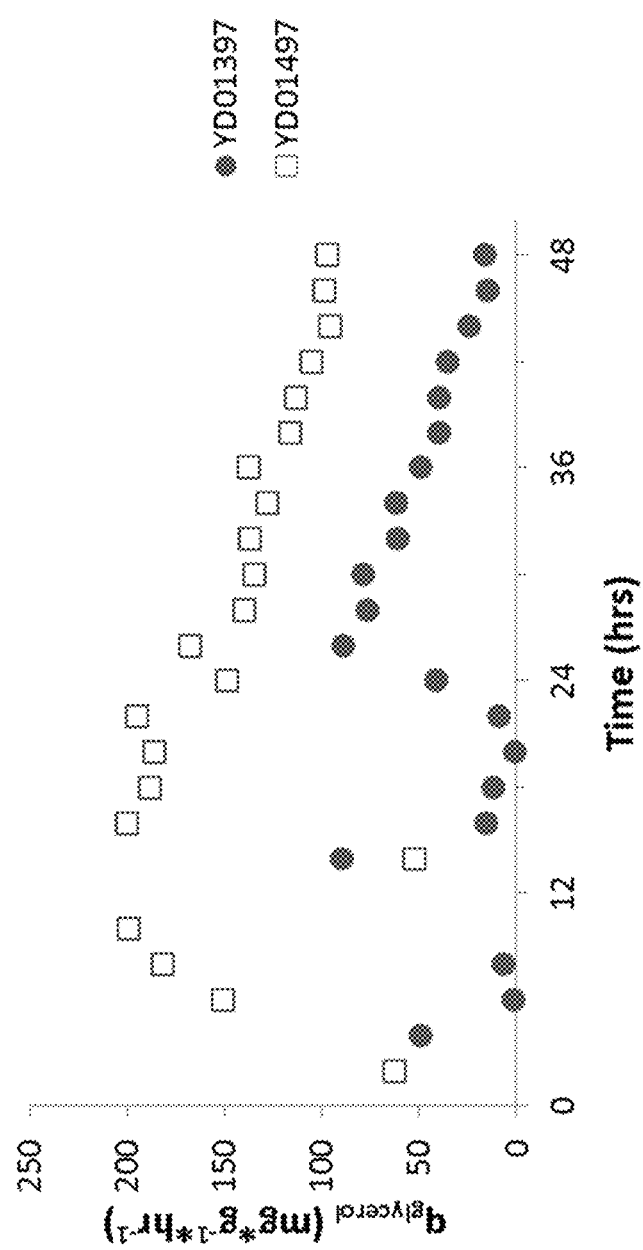
FIG. 7 Glycerol conversion per biomass for strains YD01397 and YD01437 in fermentations of synthetic medium.

FIG. 7 Glycerol conversion per biomass for strains YD01397 and YD01437 in fermentations of synthetic medium.

Comparative Experiment F

Batch Fermentation of Lignocellulosic Hydrolysate Supplemented with Glycerol Using a Strain Expressing an Exogenous Glycerol Symporter.

Yeast strain YD01437 was pre-cultured, harvested, washed and re-suspended to a biomass concentration of 50 g/l (as dry). A (1000 ml) fermenter containing (900 ml) pretreated corn stover hydrolysate (NREL batch 2, see table 1) supplemented with 12,2 g/l glycerol and adjusted to pH 5,5 with 6M KOH, was inoculated to 1.0 g/l (as dry) yeast biomass on final fermentation volume. Anaerobic fermentation was performed at 32° C. and stirred at 150 rpm.

FIG. 8 shows that strain YD01437 clearly co-consumes glucose (A), glycerol and HAc (B). However, the combination of the inhibitory effects of HAc, glycerol but likely also other compounds present in the hydrolysate mixture cause very slow and inefficient sugar conversion and yeast growth in fermentation. These inhibitory effects can be reduced by applying fed-batch fermentation, which is shown in example 1.

Example 1

Fed-Batch Fermentation of Lignocellulosic Hydrolysate Supplemented with Glycerol Using a Strain Expressing an Exogenous Glycerol Symporter.

Yeast strain YD01437 was pre-cultured, harvested, washed and re-suspended to a biomass concentration of 50 g/l (as dry) and added to an empty (1000 ml) fermenter to 1.0 g/l (as dry) yeast biomass on final fermentation volume. The fermenter was subsequently fed 93,75 hrs at a constant feed rate with 900 ml pretreated corn stover hydrolysate (NREL batch 2, see table 1) supplemented with 12,2g/l glycerol and adjusted to pH 5,5 with 6M KOH. Anaerobic fermentation was performed at 32° C. and stirred at 150 rpm.

Obtained fermentation data depicted in FIG. 9 show that from at least 6 hrs into the fermentation (the first sample taken) onward, the yeast is able to convert glucose, xylose, HAc and glycerol at approximately the rate at which it is fed to the fermenter, causing these substrates to remain relatively low during the fermentation, in contrast to the batch fermentation of Comparative experiment F. As a result of these low concentrations, the inhibitory effects of these compounds (as seen in Comparative experiment F) is significantly reduced, negating their detrimental effects on sugar resulting in dramatically improved substrate conversion levels and increased EtOH content after 120 hrs of fermentation.

Advantages: HAc, but also other substrate concentrations (C6 and C5 sugars, glycerol) are all relatively low during the fermentation, reducing their respective growth-inhibiting effects (decoupling, osmotic etc.). As compared to a batch fermentation or a traditional sugar-limited fed-batch fermentation this results in:

Enabling fermentation of hydrolysates in which the effects of HAc on the yeast's growth and survival are so severe that they result in insufficient biocatalyst activity to complete substrate conversions.

Reduced yeast pitch requirement in hydrolysates with less severe inhibitor content.

Example 2

Fed-Batch Fermentation of Lignocellulosic Hydrolysate Supplemented with Glycerol at Decreased pH.

In the experiment described in example 1, concentrations of HAc, sugars and glycerol are strongly reduced compared to the batch fermentation of Comparative experiment F. To keep the inhibitory effects of these compounds on the yeast as low as possible, ideally, these concentrations would be close to 0 g/l for the full duration of the fermentation.

To improve HAc conversion compared to the experiment in example 1 (where 2,1 g/l HAc remained unconverted), the pH of the fermentation broth is maintained lower by feeding a hydrolysate/glycerol mixture that is not pH-adjusted after enzymatic hydrolysis. The fraction of undissociated HAc in the fermentation broth available for conversion to EtOH is thereby increased, and total residual HAc subsequently decreased.

Yeast strain YD01437 is pre-cultured, harvested, washed and re-suspended to a biomass concentration of 50 g/l (as dry) and added to 3 empty (1000 ml) fermenters to 1.0 g/l (as dry) yeast biomass on final fermentation volume. Fermenters are initially fed at a constant rate of 0,20 ml/min (1,31% of final volume/hr, corresponding to a total feed time of 75 hrs) with pretreated corn stover hydrolysate (NREL batch 2, see table 1) supplemented with 12,2 g/l glycerol and adjusted to 5,5 with 6M KOH. Anoxic fermentation is performed at 32° C. and stirred at 150 rpm.

Figure 10A:
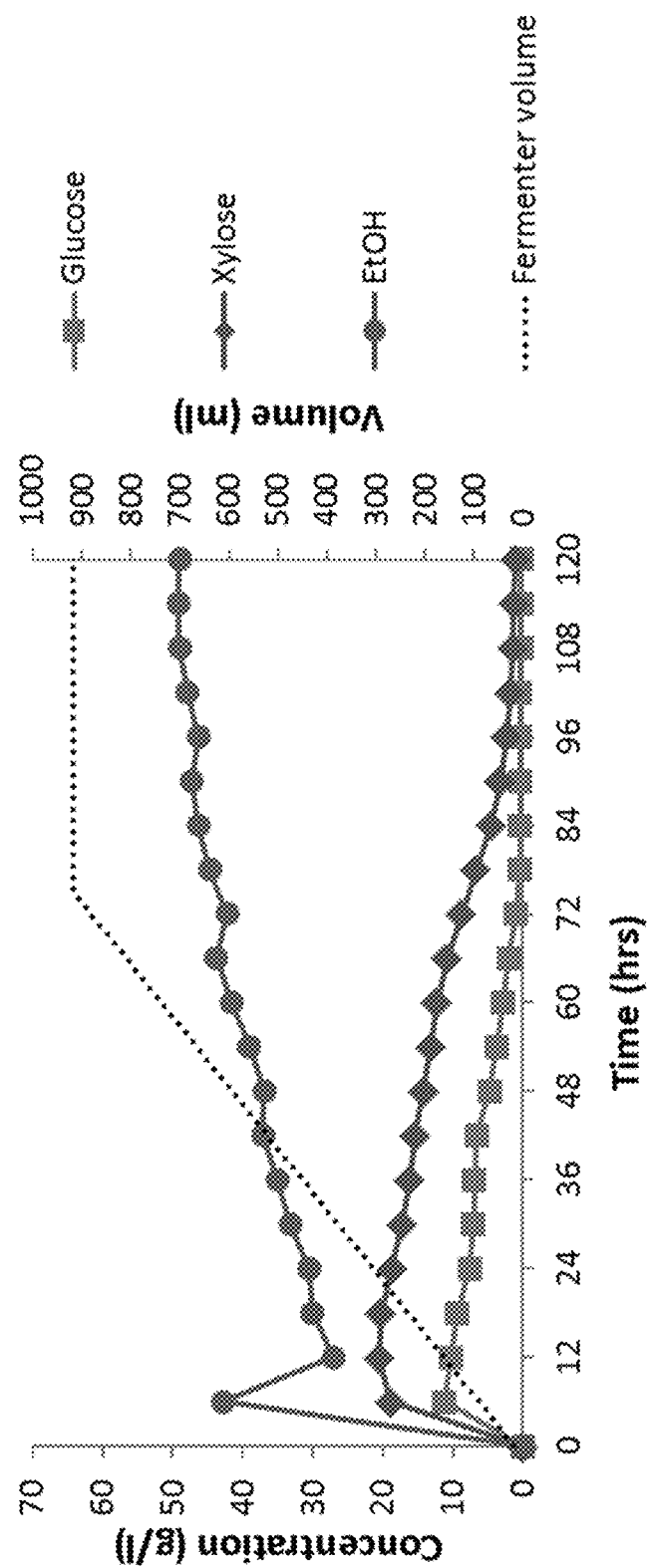
FIG. 10 Fed-batch Fermentation of YD01437 on (NREL) pretreated corn stover hydrolysate supplemented with glycerol at reduced pH; t=0-36hrs feed at pH 5.5, t=36-75hrs feed at pH 4.3. Sugar conversion and EtOH production (A), glycerol- and HAc conversion, broth pH and biomass (calculated from OD700) (B).
Figure 10B:
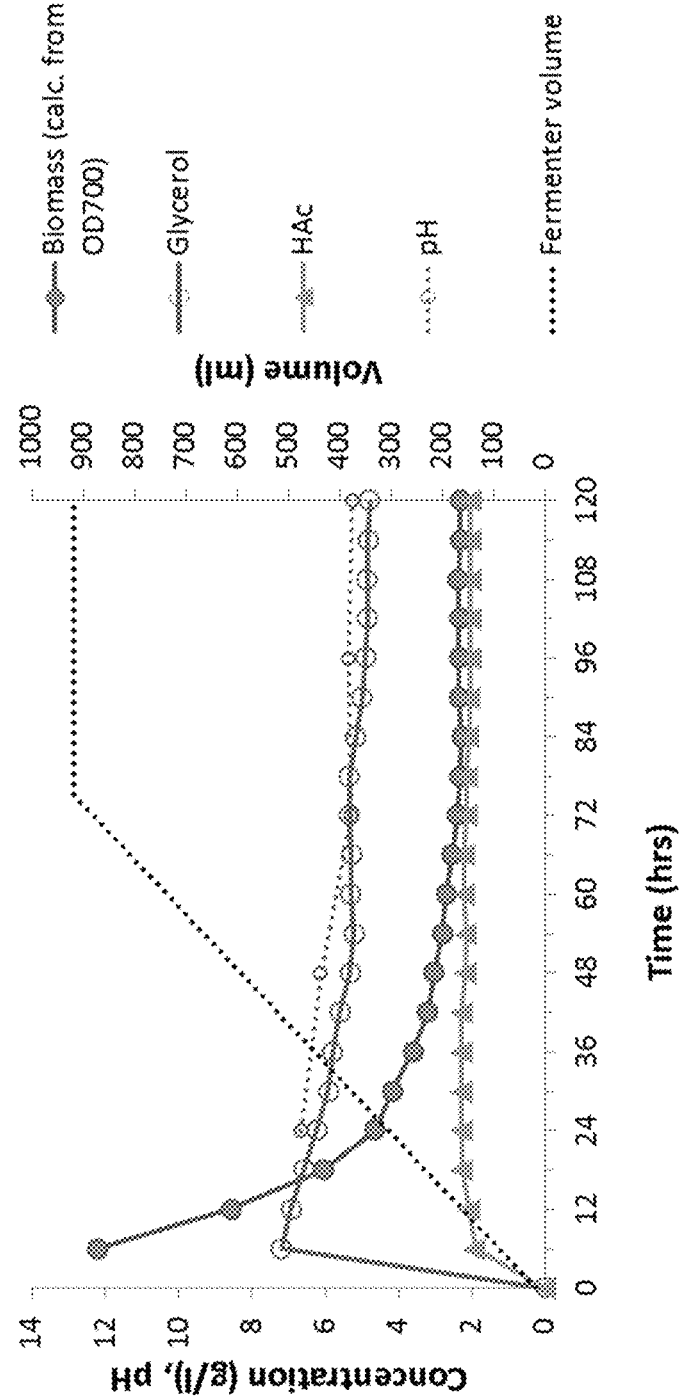
Figure 11A:
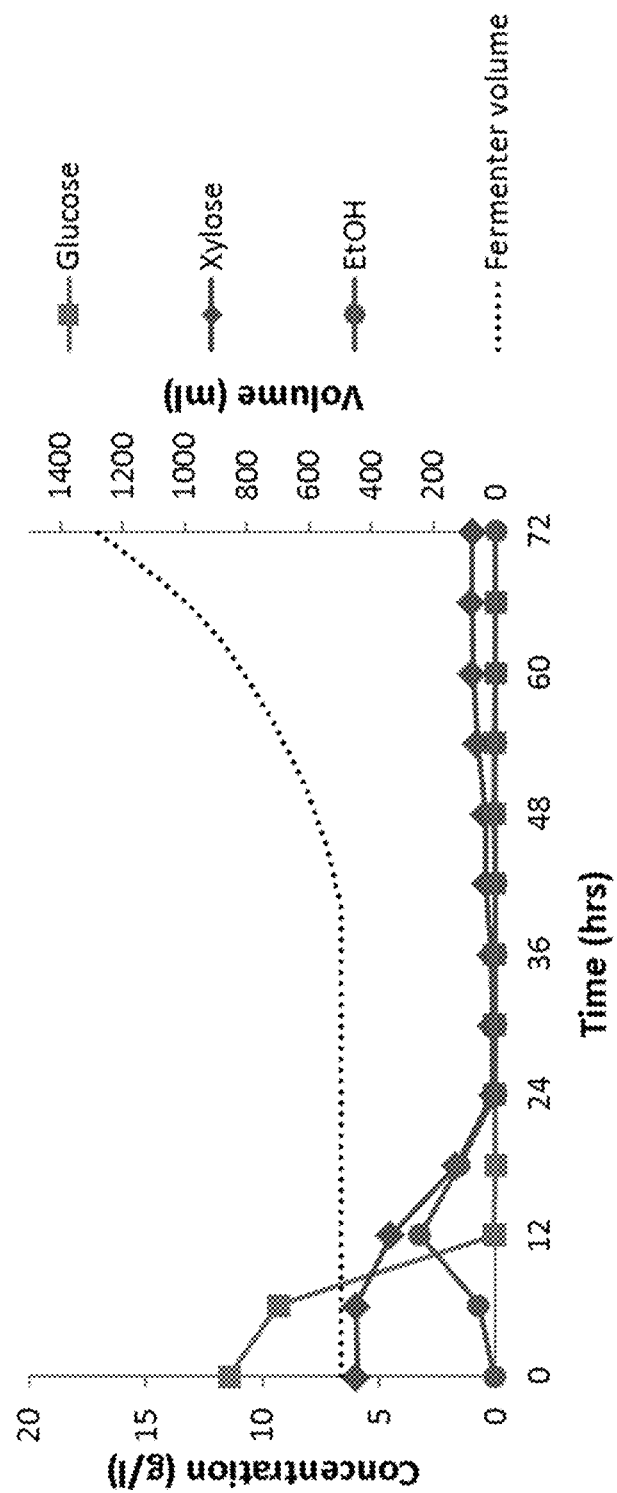
FIG. 11 FIG. 11 (A,C) Aerobic pH-regulated fed-batch propagation of strain YD01437 on (NREL) pretreated corn stover hydrolysate followed by (B,D) ph-regulated fed-batch fermentation of the same hydrolysate supplemented with glycerol. Sugar conversion and EtOH production (A), glycerol- and HAc conversion, broth pH and biomass (calculated from OD700) (B).
Figure 11B:
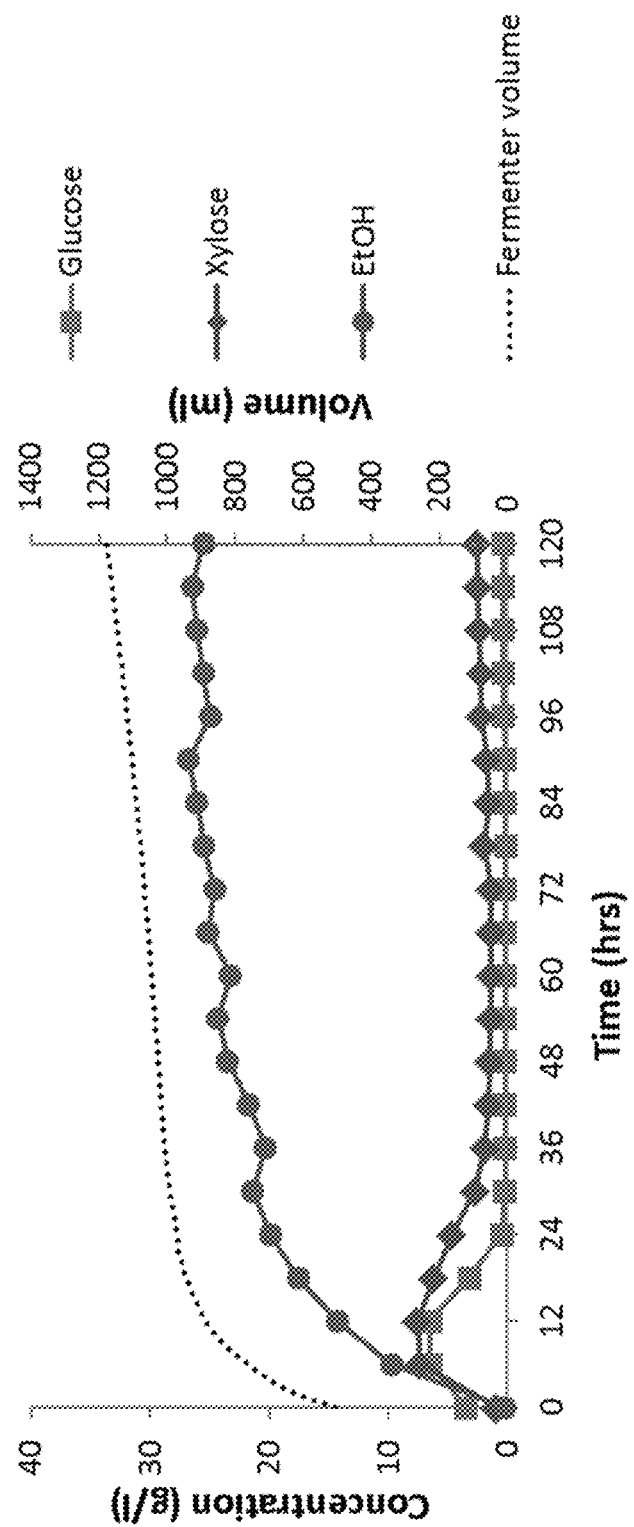
Figure 11C:
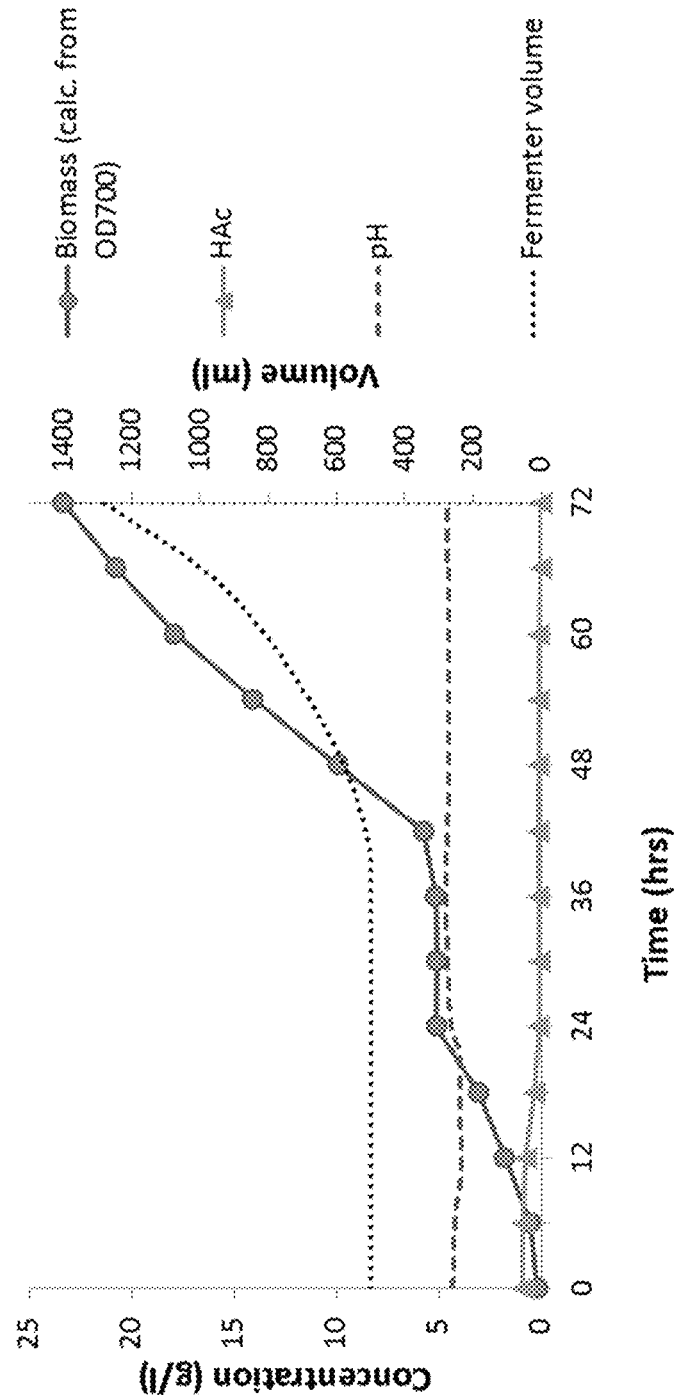
Figure 11D:
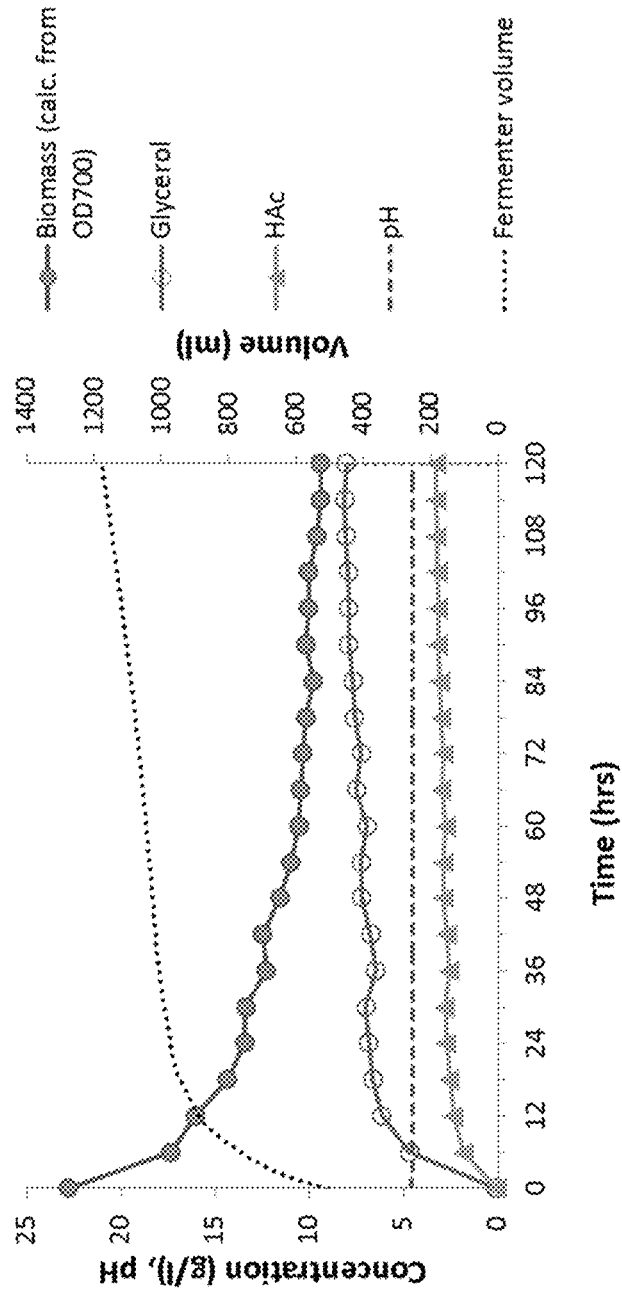

FIG. 10 shows that the addition of the non-pH adjusted feed starting from 36 hrs leads to a decrease in broth pH (B), but the fermentation still runs almost identical to the fermentation that was fed exclusively with hydrolysate/glycerol mixture at pH5,5 (example 1, FIG. 9).

Advantages: Reducing sugar losses to bacterial contaminants in the fermentation by:
  Enabling fermentation of HAc-containing lignocellulosic hydrolysates at a lower pH than the pH 5-5,5 common practice for fermentations of lignocellulosic hydrolysate. At very low HAc concentrations in the broth, fermentation can even take place at pH below pKa of HAc, which is common in traditional ($1^{st}$ generation) sugar/starch to EtOH plants as it favors yeast-over bacterial growth.
  EtOH concentration is higher throughout the fermentation compared to a sugar-limited or non-sugar limited fed-batch fermentation, and even more so compared to a batch fermentation.

These effects also decrease/remove the requirement for addition of antibiotics.

Example 3

Fed-Batch Fermentation of Lignocellulosic Hydrolysate Supplemented with Industrial Glycerol Sources.

Experiment of example 1 is repeated with a glycerol supplementation to the hydrolysate through addition of industrial byproduct streams; one with (1st generation) starch-to-EtOH 'syrup', and one with transesterification-based biodiesel 'crude glycerin' (see table 2 for compositions).

'Syrup' or 'solubles' is the concentrated liquid fraction of stillage (by evaporation), obtained from a traditional (1st generation) corn-starch-to-EtOH plant (see table 2). Glycerol sources were mixed into the hydrolysate feed at such a ratio that the molar ratio of glycerol to HAc in the obtained mixed feed is 2:1. As this caused a slight dilution of the hydrolysate, analyses of the resulting mixed feed are also shown in table 2, in the far right column. The results are shown in FIG. 11 (A to D); glycerol source: 1G syrup (A,C) and biodiesel derived glycerin (B,D).

The additional sugars and HAc that are introduced in the fermentation translate to a slightly increased EtOH titer at the end of fermentation.

Advantages:
  Stillage is directly available on-site at biorefineries that are co-located with a 1st generation EtOH plant.
  Stillage contains nutrients, from (mostly lysed) yeast from C6 fermentation, that are beneficial for yeast growth in the fermentation of lignocellulosic hydrolysate. These also include nitrogen, which will result in savings in N-source addition to the hydrolysate of up to 0,03 $/gal, depending on the initial N-content of the hydrolysate and price of the envisioned N-source (e.g. ammonia).
  Stillage contains residual sugars from C6 fermentation which will increase potential final EtOH titer for the fermentation of lignocellulosic hydrolysate.
  Stillage often contains HAc produced in the C6 fermentation which can also potentially be converted to EtOH in the fermentation of lignocellulosic hydrolysate.

'Crude glycerin' is obtained from transesterification-based biodiesel production (see table 2). It will be mixed into the hydrolysate feed at such a ratio that the molar ratio of glycerol to HAc in the obtained mixed feed is 2:1.

Advantage:
  Crude glycerol abundantly available as the main by-product of biodiesel production, generated from the transesterification of vegetable or animal fats.

and oils. It has a relatively low value due to the presence of impurities (such as methanol, salts and fatty acids) and is therefore an economically attractive source of glycerol for this application.

Crude glycerol will become increasingly available on-site as a byproduct a biorefineries that are co-located with a 1st generation EtOH plant in which biodiesel is produced from extracted corn-oil. In this process, transesterification will take place using the on-site produced EtOH instead of methanol; any residual EtOH in the crude glycerin will be also be recovered when glycerol byproduct is applied in the fermentation process described is here.
  The considerable concentration of impurities, such as salts ($K_2SO_4$ or NaCl, up to 7% w/v), that will be inhibitory in microbial conversion in processes that, for economic reasons, require utilization of the crude glycerol without/at low dilution, will be less of a problem due to the dilution in the glycerol-hydrolysate blending-ratio envisioned in the process described here (factor of 4-8×).

When applying crude glycerin as a glycerol source, fermentation rate is slightly decreased due to the introduction of impurities (salts).

Example 4

Fed-Batch Propagation and Fermentation of Lignocellulosic Hydrolysate with Glycerol with pH-Regulated Feed Profile To keep the inhibitory effects of sugars, HAc and glycerol on the yeast as low as possible, ideally, the concentrations of these compounds would be (close to) 0 g/l for the full duration of the fermentation. Although in lignocellulosic hydrolysates, sugars are generally present at higher concentrations than HAc (and supplemented glycerol), glycerol and HAc utilization are rate-limiting when applying a feed strategy aimed at keeping al (yeast-inhibiting) substrate levels low because conversion rates of glycerol and HAc (coupled through $NAD^+$-NADH cofactor utilization) are much lower than those of the sugars present in the hydrolysate. Ideally, dosing of the feed would therefore be directly coupled to the remaining HAc in the fermentation broth.

As is observed in example 2, the pH of the fermentation broth is indicative of the residual concentration of HAc. Therefore, a residual HAc-coupled feed can be automated by applying pH-regulation using (acidic) hydrolysate feed, analog to what has been described in patent application WO2014072232-A1 for pH-regulated aerobic fed-batch yeast propagation. Adding to the practicality of such a method, pH is a parameter that is already commonly (on-line) measured in (ethanolic) fermentation processes and therefore does not require large hardware-modification investments when applied at large scale.

The experiment was started by performing an aerobic pH-controlled fed-batch yeast propagation of strain YD01437 according to WO2014072232 A1. pH of the feed was not adjusted (from pH 4.3, after enzymatic hydrolysis). pH of the propagation broth was controlled at 4.5 by dosing of the lignocellulosic hydrolysate feed for 72 hrs. Aeration of the fermenter was stopped at this point, after which a portion of the propagation broth was removed from the fermenter, leaving a quantity of 500 ml broth in the fermenter (corresponding to the fermenter minimum working volume), containing 23.4 g/l (as dry) yeast biomass.

Figure 12:
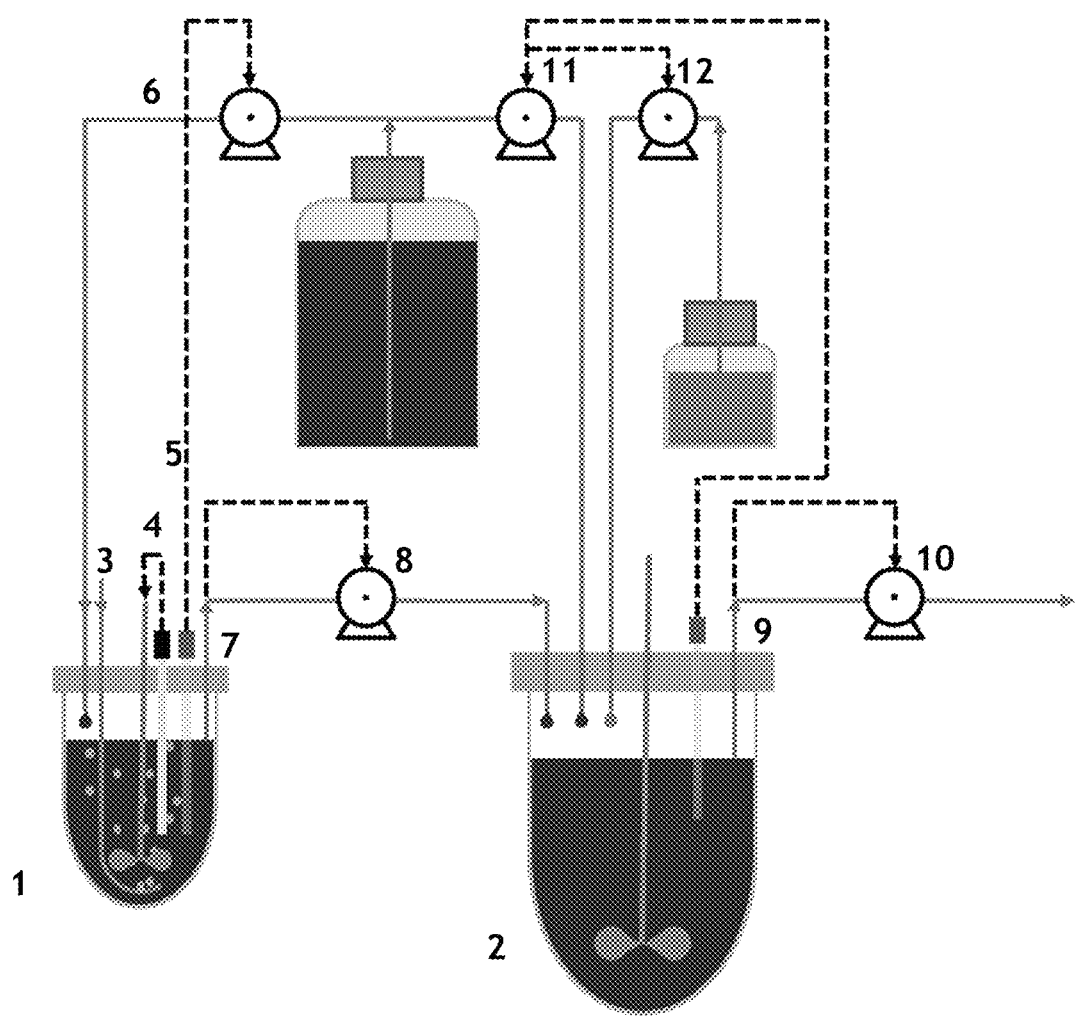
FIG. 12 Schematic representation of the pH-regulated continuous yeast propagation and fermentation system of example 6.
Figure 13A:
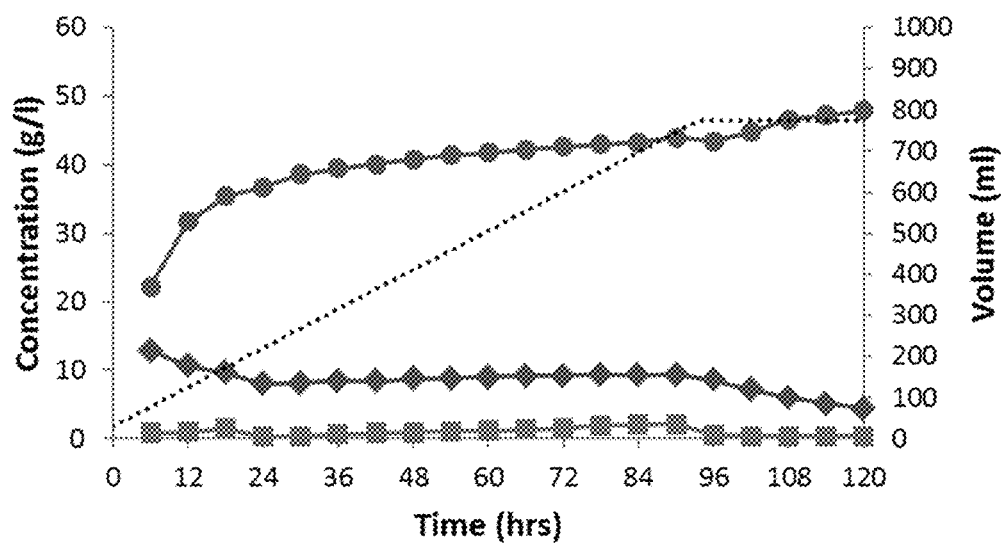
FIG. 13 Fed-batch Fermentations of YD01437 on (NREL) pretreated corn stover hydrolysate supplemented with glycerol; No recycled broth in the starting volume (A,D), 30 ml (B,E) and 90 ml (C,F) recycled broth in the starting volume. The following signs are used in A, B, C: sugar conversion glucose (--*--) and xylose (--+--) and EtOH (--*--), fermentor volume ( . . . ) and in D, E, F: glycerol (--*--) (--*--), pH (--·--) biomass (calculated from OD600) (--*--), fermentor volume ( . . . ).
Figure 13B:
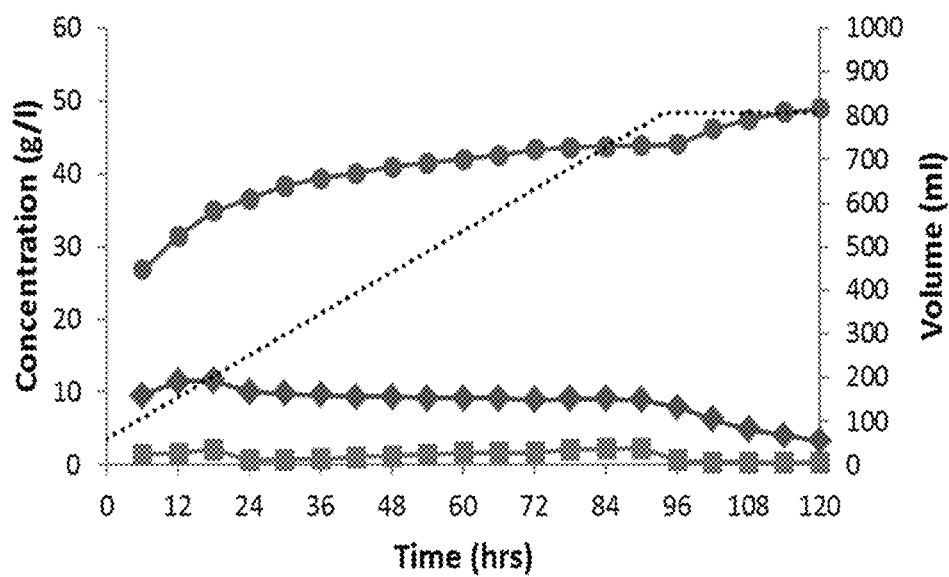
Figure 13C:
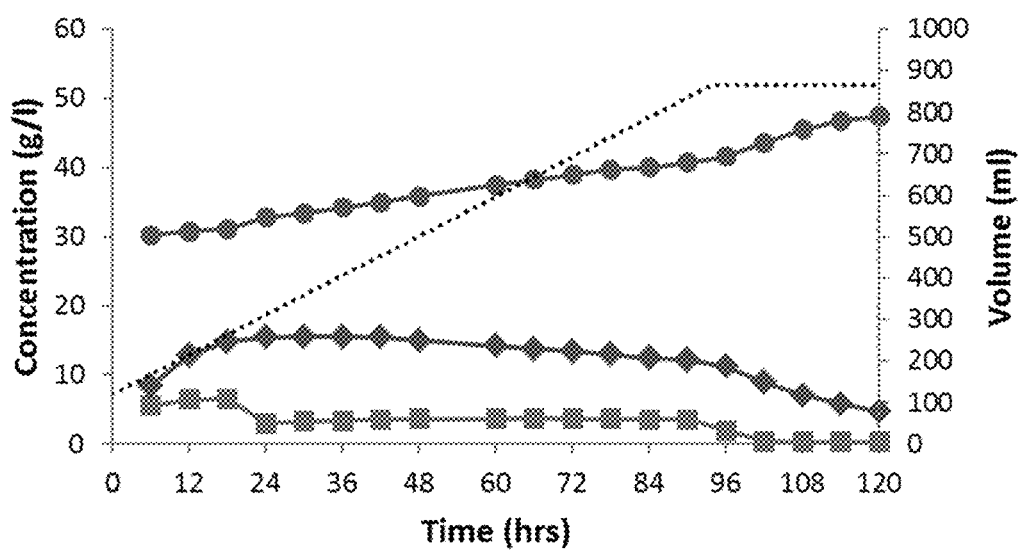
Figure 13D:
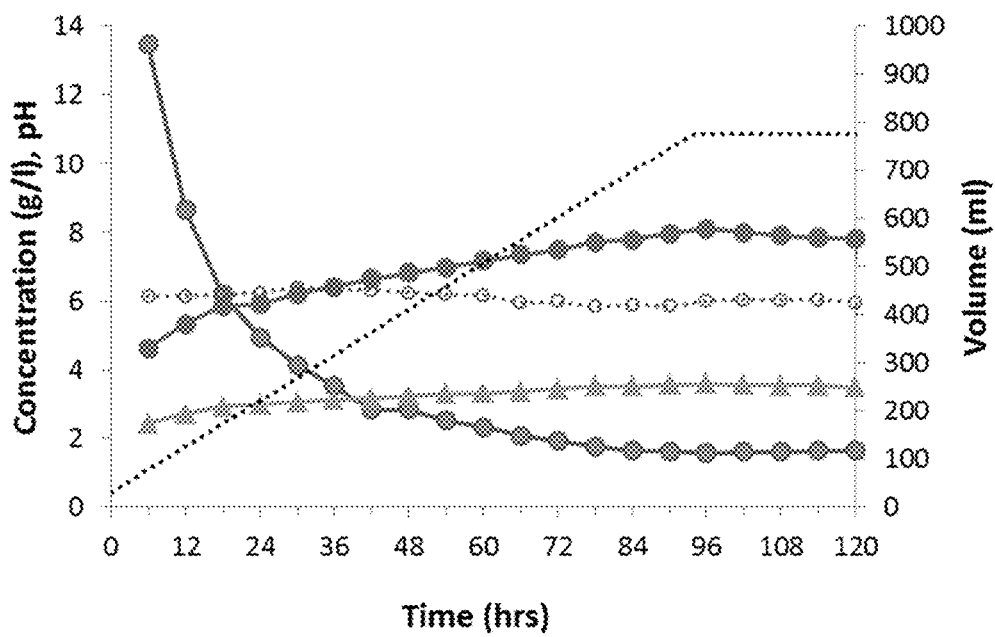
Figure 13E:
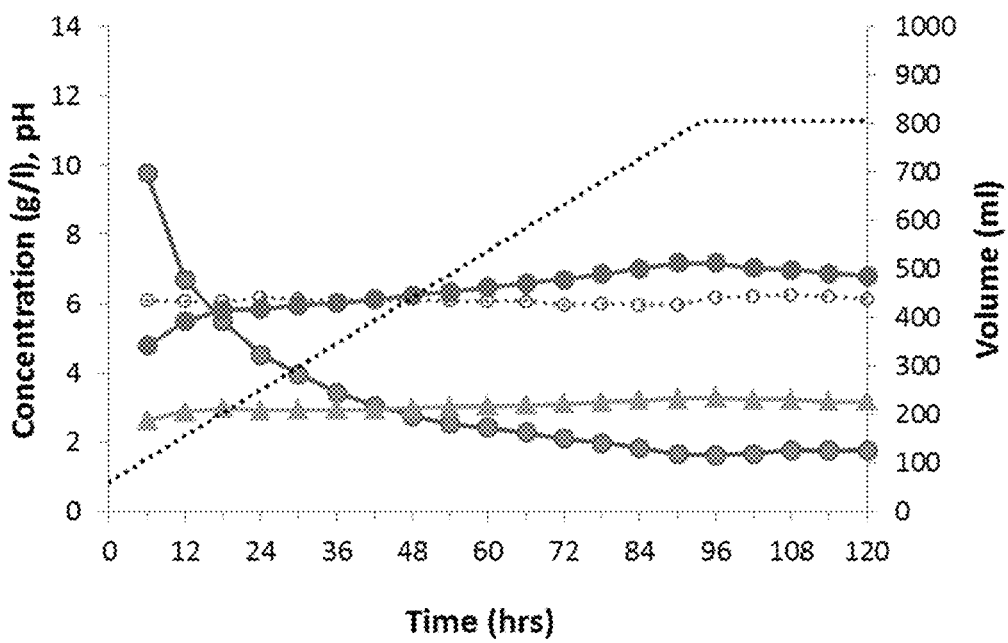
Figure 13F:
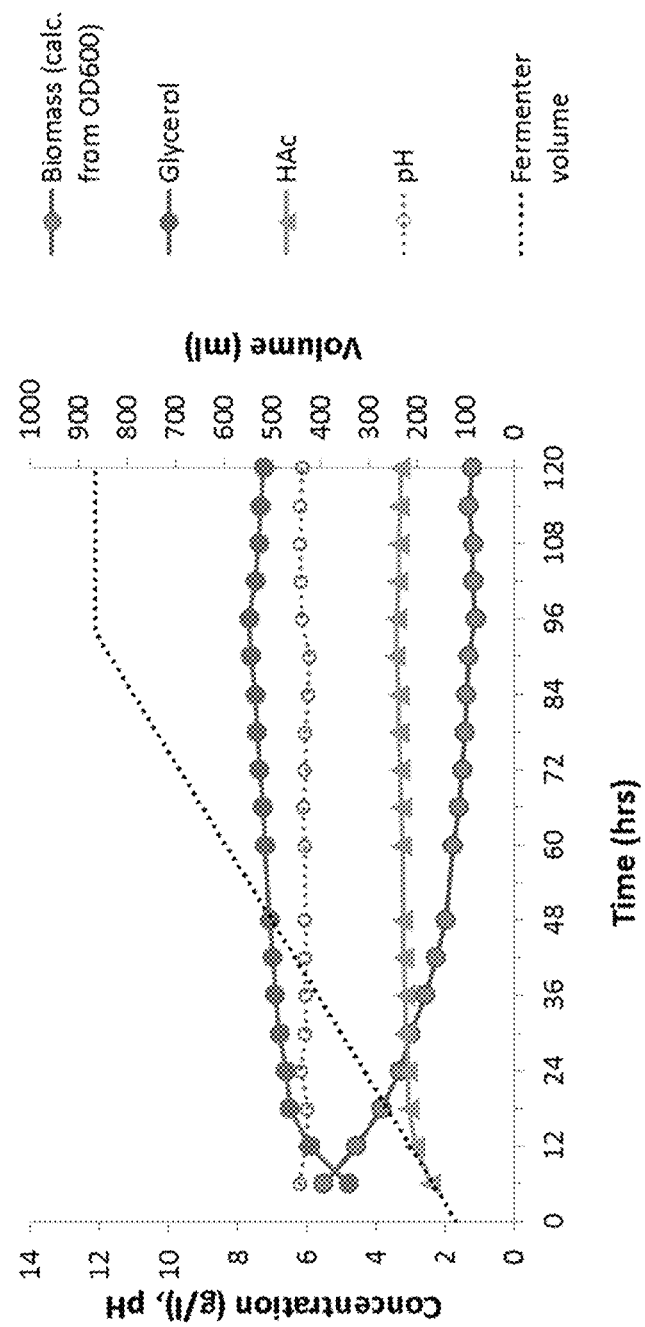

After the switch to anoxic conditions, pH of the fermentation broth was controlled at 4.5 by dosing of a mixture of the lignocellulosic hydrolysate and glycerol, in which the molar ratio of glycerol to HAc was 2:1. The pH of the feed was also not adjusted (from pH 4.3). The results are shown in FIG. 12. In this FIG. 12, (A,C) is Aerobic pH regulated fed-batch propagation of strain YD01437 on (NREL) pretreated corn stover hydrolysate and (B,D) is pH-regulated fed-batch fermentation of the same hydrolysate supplemented with glycerol. Sugar conversion and EtOH production (A), glycerol- and HAc conversion, broth pH and biomass (calculated from OD700) (B).

Example 5

Fed-Batch Fermentation of Lignocellulosic Hydrolysate with Glycerol Recycling

Peak concentrations of HAc, glycerol and sugars at the early stages of fermentation when feeding a hydrolysate/glycerol-mixture to a relatively low volume of broth can be prevented by increasing the batch-phase volume, effectively decreasing the relatively high dilution rates at the start of feeding. An increase of batch phase volume can be achieved in 2 ways:

By performing propagation process with lower final yeast biomass concentration, so a larger volume of propagation broth is used in the fermentation. This is undesirable from an economic point of view however, as this would require correspondingly larger propagators, leading to increased CAPEX.

Applying dilution of the propagation broth. This is typically done in industrial fermentations of lignocellulosic hydrolysate by addition of process water to the fermenter. This is, however, also undesirable as this introduces additional water into the system, which increases total fermentation volume (requiring larger fermenters and increased CAPEX), lowers final EtOH titer (lower (energy) efficiency in distillation, leading to increased OPEX. Additionally, the dilution water will need to be processed downstream of distillation (evaporation/anaerobic digester), leading to further production cost increases (CAPEX & OPEX).

A unique feature of the fermented broth from a fermentation process using HAc-converting strains in combination with a feeding strategy as described here is that it has a significantly reduced HAc content (compared to the unfermented hydrolysate). This allows (part oh the fermented broth, or distilled fermentation broth (stillage) to be recycled into the batch-phases of subsequent propagation and fermentation cycles without introducing inhibitory concentrations of HAc.

If this fermented broth also contains residual glycerol, it will be recycled in the fraction that is applied in a subsequent fermentation cycle, lowering the required glycerol supplementation of the hydrolysate, thereby improving the economics of the conversion process.

The experiment was started by performing a pH-controlled aerobic fed-batch yeast propagation of strain YD01437 on pretreated corn stover hydrolysate batch 3 (table 1) according to WO2014072232 A1, with a fixed dilution rate of 0,06 $hr^{-1}$. pH of the feed was adjusted (from 4.3) to 5.5, after enzymatic hydrolysis). Propagation broth was harvested from the fermenter after 50 hrs, at which approximately 800 ml of the hydrolysate had been fed. At this point, the propagation broth contained 34 g DCW/l yeast biomass, while concentrations of all fermentable C-sources (glucose, xylose, HAc and glycerol) were >1 g/l.

Aliquots of 30 ml fermentation broth (containing 1,0 g DCW yeast biomass) were transferred to (1000 ml) fermenters containing 0, 30 and 90 ml recycled fermentation broth respectively (with 0,4 g/l glucose, 0,5 g/l xylose, 1,7 g/l HAc, and 2,8 g/l glycerol as fermentable C-sources, as well as 47,5 g/l EtOH and a pH of 7,7). As this broth had been filtrated (0,2 μm pore-size) after harvesting it from the fermenter, both to enable storage (at 4° C.) without spoilage and to enable biomass monitoring through OD measurement in the subsequent fermentation, this broth contained no yeast activity from the preceding fermentation. Fermenters were subsequently fed with a total 745 ml pretreated corn stover hydrolysate (NREL batch 3, see table 1) supplemented with 14,3 g/l glycerol and adjusted to pH 5,5 with 6M KOH, over 94 hrs at a constant feed rate. Anaerobic fermentation was performed at 32° C. and the broth was stirred at 150 rpm.

The results are presented in FIG. 13. FIG. 13 shows that there is no adverse effect of increasing the batch volume 2× by addition of recycled fermentation broth (A,D vs B,E). Even when increasing the batch volume with a factor 4, the effect of diluting out the yeast biomass is limited, resulting in a slightly decreased sugar conversion rate. In fermentations where reduction of acetic acid concentration by conversion to EtOH is more challenging (e.g. more toxic hydrolysate), the risk of overfeeding exists. When feeding more HAc to the broth than the yeast is able to convert, the residual HAc leads to high concentration in the fermentation broth as there is only a small liquid volume in the fermenter and hence this residual HAc is not diluted out much. High concentration of HAc in the broth subsequently inhibits its conversion to EtOH by the yeast, which can result in a stuck or at least sluggish fermentation. By adding detoxified broth from a previous fermentation to the fermenter prior to feeding, any HAc fed to the fermenter that is not directly converted is diluted out more strongly, effectively dampening the inhibitory effects of overfeeding, and allowing the conversion of HAc in the broth to continue and possibly catch up later in the fermentation, when the dilution factor becomes progressively smaller.

Example 6

Coupled Continuous Propagation and Fermentation System

A schematic setup for this experiment is depicted in FIG. 12). The experiment is started by filling 2 fermenters (FIG. 12: 1-2) for ⅕ of their final volume with (NREL pretreated corn stover, batch 2) hydrolysate (see table 1) and ⅘ volumes of water. The medium in fermenter 1 is supplemented with nutrients, the medium in fermenter 2 is supplemented with stillage (see table 2) to such an extent that the molar ratio of glycerol to HAc in both fermenters is 2:1).

Fermenter 1 is inoculated to a concentration of approximately 0,02 g/l of freshly pre-cultured strain YD01437 and aerated at 1 wm (FIG. 12: 3). Dissolved oxygen is controlled at 20% through a stirrer cascade (150-500 RPM) (FIG. 12: 4). The yeast utilizes available c-sources from the diluted hydrolysate for growth and maintenance. Continuous conversion of the HAc causes the broth pH to rise (FIG. 12: 5). pH is subsequently maintained at 4,5 by dosing of (acidic) hydrolysate (FIG. 12: 6) to the fermenter which effectively results in a pH-regulated feed which will stabilize at an average dilution rate of approximately 0.09 hr$^{-1}$. Although additional hydrolysate is added to the fermenter, the concentration of HAc in the broth is maintained close to 0 g/l allowing the yeast to grow efficiently. Concentration of yeast biomass in the hydrolysate gradually increases to approximately 46 g/l (as dry). A maximum level indicator in fermenter 1 (FIG. 12: 8) triggers a pump that provides a continuous flow of propagation broth from fermenter 1 to fermenter 2 (FIG. 12: 2).

The yeast propagated in fermenter 1 (anaerobically) converts glucose, xylose, glycerol and HAc in fermenter 2.

A maximum level indicator in fermenter 2 (FIG. 12: 9) will triggers a pump that provides a continuous flow of fermented broth out of fermenter 2 (FIG. 12: 10). In an industrial setting, such a stream would be fed to the distillation system, optionally via a buffer tank.

The continuous influx of freshly propagated yeast from fermenter 1 (FIG. 12: 8) increases the yeast concentration in fermenter 2 to the extent that a degree of glycerol and HAc conversion is achieved that increases the pH of the broth to the level of the setpoint that triggers 2 separate feeds to fermenter 2; hydrolysate (FIG. 12: 11) and stillage (FIG. 12: 12). The ratio between these feeds is set in such a way that the molar ratio of glycerol to HAc in the combined feed influx (hydrolysate+stillage) is 2:1.

In this combined continuous propagation and fermentation system, an equilibrium is automatically established between fermentation residence time and the quantity of yeast in the fermentation section. The flux of yeast biomass can manually be adjusted by changing fermenter 1 working volume; (by adjusting the height of level sensor (FIG. 12: 7)); smaller propagation volume will decrease yeast output.

The degree of HAc conversion can manually be adjusted through changing the pH control setting of fermenter 2; decreasing this setting decreases the fraction of HAc that has to be converted to trigger the (acidic) feed.

LITERATURE

Van Dijken and Scheffers (1986) "Redox balances in the metabolism of sugars by yeasts". FEMS Microbiology Letters Volume 32. Issue 3-4. pages 199-224;

Sonderegger et al (2004) "Metabolic Engineering of a Phosphoketolase Pathway for Pentose Catabolism in *Saccharomyces cerevisiae*". AEM 70(5). 2892-2897;

Guadalupe Medina V. Almering M J. van Maris A J. Pronk J T (2009) "Elimination of glycerol production in anaerobic cultures of *Saccharomyces cerevisiae* engineered for use of acetic acid as electron acceptor." Appl Environ Microbiol. pages 190-195;

Yu et al (2010) "Engineering of glycerol utilization pathway for ethanol production by *Saccharomyces cerevisiae*". Bioresour. Technol. 101(11):4157-4161;

Yu et al (2012) "Improvement of Ethanol Yield from Glycerol via Conversion of Pyruvate to Ethanol in Metabolically Engineered *Saccharomyces cerevisiae*", Appl. Biochem. Biotechnol. February 2012, Volume 166(4) pages 856-865

Lee and Dasilva (2006) "Application of sequential integration for metabolic engineering of 1.2-propanediol production in yeast". Metab. Eng. 8(1):58-65;

Luttik et al. (2000) "The *Saccharomyces cerevisiae* ICL2 gene encodes a mitochondrial 2-methylisocitrate lyase involved in propionyl-coenzyme A metabolism", J. Bacteriol. Dec. 2000, 812 (24) p. 7000-7013.

The invention claimed is:

1. A process for producing ethanol, the process comprising:
    a) inoculating a diluted lignocellulosic hydrolysate, in a reactor, with a yeast that is capable of consuming sugar, glycerol and acetic acid and aerobically propagating the yeast to generate a propagation broth;
    b) fermenting the diluted lignocellulosic hydrolysate anaerobically with at least a portion of the propagation broth in a fed batch mode to generate a fermentation broth, wherein the pH of the fermentation broth is controlled by adding a mixture comprising lignocellulosic hydrolysate and glycerol to the reactor in amounts sufficient to maintain a constant pH in the fermentation broth, in which mixture the molar ratio of glycerol to acetic acid is in the range of 1.8 to 2.2;
    c) after sufficient fermentation time, isolation of ethanol from the reactor;
    d) optionally keeping the remaining fraction after isolation of c) as spent broth; and
    e) optionally using a part of the spent broth of d) to dilute the lignocellulosic hydrolysate of a);
    wherein the yeast is genetically modified comprising:
        one or more nucleotide sequence encoding a heterologous NAD+-dependent acetylating acetaldehyde dehydrogenase (E.C. 1.2.1.10);
        one or more nucleotide sequence encoding a homologous or heterologous acetyl-CoA synthetase (E.C. 6.2.1.1);
        one or more nucleotide sequence encoding a heterologous glycerol dehydrogenase (E.C. 1.1.1.6); and
        one or more nucleotide sequence encoding a homologous or heterologous dihydroxyacetone kinase (E.C. 2.7.1.28 or E.C. 2.7.1.29).

2. The process of claim 1, wherein the added lignocellulosic hydrolysate comprises glycerol originating from a starch or sugar based ethanol product plant or a biodiesel plant.

3. The process of claim 1, wherein the addition of lignocellulosic hydrolysate comprising glycerol is commenced when the glucose concentration in reactor is 2 g/l or lower.

4. The process of claim 1, wherein the remaining part of the spent broth of d) is kept as spent broth, and is used in b).

5. The process of claim 1, wherein the yeast cell is capable of consuming xylose in the lignocellulosic hydrolysate, optionally substantially all xylose.

6. The process of claim 1, wherein the yeast cell has a deletion or disruption of one or more endogenous nucleotide sequence encoding a glycerol 3-phosphate phosphohydrolase and/or encoding a glycerol 3-phosphate dehydrogenase gene.

7. The process of claim 1, wherein the yeast cell expresses an exogenous glycerol symporter.

8. The process of claim 1, wherein during the process no base needs to be added to the mixture in the reactor.

9. The process of claim 1, wherein the yeast cell is capable of metabolizing organic acid, optionally of metabolizing acetic acid.

10. The process of claim 1, wherein the concentration of acetic acid in the fed batch reactor is 30 g/l or less.

11. The process of claim 10, wherein the lignocellulosic hydrolysate is fed into the fed batch reactor at a rate of from 0.01 $h^{-1}$ (vol/vol) to 0.10 $h^{-1}$ (vol/vol).

12. The process of claim 1, wherein the pH in the reactor in fed batch mode is pH 4 to pH 7.

13. The process of claim 1, wherein the process is an anaerobic or anoxic fed-batch fermentation process in which the pH of the fermentation broth in the reactor is higher than the pH of the feed.

14. The process of claim 1, wherein the yeast cell can anaerobically ferment at least one C6 sugar and at least one C5 sugar.

15. The process of claim 1, wherein to the fermentation process, a propagation process is added.

16. The process of claim 1, wherein the process or processes are continuous.

17. The process of claim 16, which is a coupled continuous propagation and fermentation process.

18. The process of claim 1, wherein the lignocellulosic hydrolysate is added in a fed batch mode in a fed batch reactor.

* * * * *